US012678407B2

(12) United States Patent
Kim et al.

(10) Patent No.: US 12,678,407 B2
(45) Date of Patent: *Jul. 14, 2026

(54) COMPOSITE FORMULATION COMPRISING SITAGLIPTIN AND DAPAGLIFLOZIN AND PREPARATION METHOD THEREFOR

(71) Applicant: HANMI PHARM. CO., LTD., Hwaseong-si (KR)

(72) Inventors: Bo Sik Kim, Seoul (KR); Jin Wook Tak, Hwaseong-si (KR); Jung Hyun Cho, Hwaseong-si (KR); Ho Taek Im, Yongin-si (KR); Yong Il Kim, Gwacheon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 481 days.

This patent is subject to a terminal disclaimer.

(21) Appl. No.: 18/015,278

(22) PCT Filed: Apr. 29, 2021

(86) PCT No.: PCT/KR2021/005474
§ 371 (c)(1),
(2) Date: Jan. 9, 2023

(87) PCT Pub. No.: WO2022/010078
PCT Pub. Date: Jan. 13, 2022

(65) Prior Publication Data
US 2023/0255890 A1 Aug. 17, 2023

(30) Foreign Application Priority Data
Jul. 10, 2020 (KR) ........................ 10-2020-0085679

(51) Int. Cl.
| | |
|---|---|
| *A61K 9/16* | (2006.01) |
| *A61K 9/20* | (2006.01) |
| *A61K 31/4985* | (2006.01) |
| *A61K 31/7034* | (2006.01) |

(52) U.S. Cl.
CPC ........ *A61K 9/1617* (2013.01); *A61K 31/4985* (2013.01); *A61K 31/7034* (2013.01)

(58) Field of Classification Search
CPC .............. A61K 9/1617; A61K 31/4985; A61K 31/7034; A61K 9/2077
See application file for complete search history.

(56) References Cited

U.S. PATENT DOCUMENTS

| 2012/0071403 | A1 | 3/2012 | Strumph et al. |
|---|---|---|---|
| 2013/0224296 | A1* | 8/2013 | Narang ................ A61K 9/2009 514/23 |
| 2022/0287980 | A1 | 9/2022 | Ito et al. |
| 2023/0033410 | A1 | 2/2023 | Chang et al. |
| 2023/0149314 | A1* | 5/2023 | Tak ...................... A61K 9/2095 424/470 |
| 2024/0325311 | A1* | 10/2024 | Tak ...................... A61K 9/2077 |

FOREIGN PATENT DOCUMENTS

| CN | 114828831 A | 7/2022 |
|---|---|---|
| CN | 115297847 A | 11/2022 |
| IN | 201711006267 A | 8/2018 |
| JP | 2013-538814 A | 10/2013 |
| JP | 2015-509519 A | 3/2015 |
| JP | 2019-172672 A | 10/2019 |
| JP | 7523545 B2 | 7/2024 |
| KR | 10-2016-0111237 A | 9/2016 |
| KR | 10-2018-0079176 A | 7/2018 |
| KR | 10-2019-0130432 A | 11/2019 |
| WO | 2008/002824 A1 | 1/2008 |
| WO | 2018/097570 A2 | 5/2018 |
| WO | 2018/124497 A1 | 7/2018 |
| WO | WO 2018124497 * | 7/2018 |

OTHER PUBLICATIONS

Jabbour et al; Dapagliflozin is effective as add-on therapy to sitagliptin with or without metformin: A 24-week, multicenter, randomized, double-blind, placebo-controlled study; Diabetes care, vol. 37, Mar. 2014. (Year: 2014).*
Drug label for Januvia®. Published by FDA, Approval 2006. (Year: 2006).*
Chinese Office Action dated Nov. 21, 2023 in Chinese Application No. 202180048885.0.
"Novel Direct Compression Tablet Aids", Shanghai Chemicals, 1987, vol. 12, No. 3, pp. 59-62 (4 pages total).
Extended European Search Report issued Jun. 24, 2024 in European Application No. 21838880.9.
Arne W. Hölzer, et al., "Evaluation of Sodium Stearyl Fumarate as a Tablet Lubricant", International Journal of Pharmaceutics, 1979, vol. 2, pp. 145-153 (9 pages total).
Jinjiang Li, et al., "Lubricants in Pharmaceutical Solid Dosage Forms", Lubricants, 2014, vol. 2, 21-43 (23 pages total).
Office Action issued Dec. 17, 2024 in Japanese Application No. 2023-501142.
International Search Report for PCT/KR2021/005474 dated Aug. 4, 2021 [PCT/ISA/210].
Office Action issued May 14, 2024 in Chinese Application No. 202180048885.0.

* cited by examiner

*Primary Examiner* — Mina Haghighatian

(74) *Attorney, Agent, or Firm* — Sughrue Mion, PLLC

(57) ABSTRACT

Provided are a composite formulation including sitagliptin and dapagliflozin and a method of preparing the same.

13 Claims, 15 Drawing Sheets

FIG. 1

COMPARISON OF APPEARANCE OF FLAKE AND TABLET ACCORDING TO
PRESENCE OR ABSENCE OF MAGNESIUM STEARATE

FIG. 2

| COMPOSITE TABLET OF SITAGLIPTIN AND EXCIPIENT OTHER THAN LACTOSE | COMPOSITE TABLET OF SITAGLIPTIN AND LACTOSE |
|---|---|
| | |

FIG. 3

COMPARISON OF PRODUCTIVITY ACCORDING TO
QUANTITY OF SODIUM STEARYL FUMARATE (PRUV®)

| | COMPARATIVE EXAMPLE 6 | EXAMPLE 4 |
|---|---|---|
| COMPARISON OF TABLET APPEARANCE OF AFTER TABLETING | | |
| TIME FOR DISCHARGING GRANULES (OF 420 G) | 43 MINUTES | 24 MINUTES |

FIG. 10

COMPARISON OF PRODUCTIVITY ACCORDING TO
QUANTITY OF SODIUM STEARYL FUMARATE (PRUV®)

| | EXAMPLE 6 | EXAMPLE 10 | EXAMPLE 11 |
|---|---|---|---|
| APPEARANCE | | | |
| THICKNESS (mm) | 5.42 ± 0.06 | 5.47 ± 0.05 | 5.50 ± 0.04 |
| EXPANSION RATE (%) | 0.37 | 1.30 | 1.85 |
| | COMPARATIVE EXAMPLE 9 | COMPARATIVE EXAMPLE 10 | COMPARATIVE EXAMPLE 11 |
| APPEARANCE | | | |
| THICKNESS (mm) | 5.41 ± 0.05 | 5.44 ± 0.07 | 5.67 ± 0.07 |
| EXPANSION RATE (%) | 0.19 | 0.74 | 5.00 |

COMPARISON OF FLAKE APPEARANCE DURING
DRY GRANULATION PROCESS

| | EXAMPLE 9 | COMPARATIVE EXAMPLE 12 |
|---|---|---|
| FLAKE APPEARANCE | | |

COMPOSITE FORMULATION COMPRISING SITAGLIPTIN AND DAPAGLIFLOZIN AND PREPARATION METHOD THEREFOR

CROSS REFERENCE TO RELATED APPLICATIONS

This application is a National Stage of International Application No. PCT/KR2021/005474 filed Apr. 29, 2021, claiming priority based on Korean Patent Application No. 10-2020-0085679 filed Jul. 10, 2020.

TECHNICAL FILED

The present application relates to a composite formulation including sitagliptin and dapagliflozin and a method of preparing the same, and more particularly, to a composite formulation which has excellent productivity, dissolution rate, stability, and compounding compatibility, and a method of preparing the same.

BACKGROUND ART

In general, type 2 diabetes patients are accompanied by being overweight, abdominal obesity, and high blood pressure, and thus diabetes is known as a disease that causes secondary chronic diseases or metabolic syndromes, such as hypertension, hyperlipidemia, myocardial infection, and stroke. According to the medical guidelines of the Korean Diabetes Association, combined drug therapy is actively recommended to enhance improvement of symptoms. In particular, the combined use of DPP-4 inhibitor drugs and SGLT-2 inhibitor drugs has recently been proven by academia to have excellent efficacy in the treatment of diabetes, and even three-drug treatment with metformin is also under research.

Sitagliptin (Product name: JANUVIA tablet) is a dipeptidyl peptidase-4 (DPP-4) inhibitor drug, and its compound name is (R)-3-amino-1-(3-(trifluoromethyl)-5,6-dihydro-[1,2,4]triazole[4,3-a]pyrazin-7(8H)-yl)-4-(2,4,5-trifluorophenyl)butan-1-one. Sitagliptin regulates blood sugar by inhibiting the breakdown of gastrointestinal hormones called incretins to enable the incretins, which regulate insulin and glucagon, to function well in the body. It is known that when sitagliptin is orally administered to a patient with type 2 diabetes, HbA1c levels significantly decline, and fasting blood sugar and postprandial blood sugar levels decline.

Dapagliflozin (Product name: FORXIGA tablet) is a sodium-glucose linked transporter 2 (SGLT-2) inhibitor drug, and its compound name is (2S,3R,4R,5S,6R)-2-[4-chloro-3-(4-ethoxybenzyl)phenyl]-6-(hydroxymethyl)tetrahydro-2H-pyran-3,4,5-triol. Dapagliflozin selectively inhibits SGLT2 in the kidneys and increases the excretion of glucose in the urine, thereby improving insulin sensitivity and delaying the onset of diabetic complications, and thus allowing plasma glucose levels to be normalized. Dapagliflozin is currently available on the market by the original developer AstraZeneca AB, in the form of tablets (FORXIGA™ tablet) including dapagliflozin propylene glycol hydrate as an active ingredient.

Sitagliptin and dapagliflozin have the main effect of blood sugar reduction without a risk of low blood sugar. In addition, sitagliptin has the effects of protecting pancreatic beta cells and increasing GLP-1, and dapagliflozin has weight loss and blood pressure reduction effects, and has also been introduced with clinical results wherein a combination of two active ingredients has a synergistic effect. In addition, in the case of diabetic patients, as diabetes progresses, it becomes difficult to control blood sugar, resulting in complications. Specifically, elderly diabetic patients are more likely to suffer from high blood pressure, obesity, and hyperlipidemia. Due to these characteristics of diabetic patients, medication compliance is a very crucial factor, and a reduction in medication compliance not only lowers a patient's quality of life, but also reduces a patient's treatment rate, increasing personal medical expenses and worsening insurance finances. Therefore, it is necessary to develop a composite formulation including sitagliptin and dapagliflozin.

However, the development of the composite formulation has not yet been attempted due to numerous problems to be overcome in order to secure proper productivity, dissolution rate, and stability. For sitagliptin as an active ingredient, there are problems in which the active ingredient is contained in a large amount per tablet and punch sticking is liable to occur during a production process because the active ingredient has viscosity. In addition, dapagliflozin as an active ingredient has poor productivity because it has a large volume even in a small amount due to low density, and has a problem of difficulty ensuring formulation productivity because layer separation from other active ingredients and excipients, and agglomeration due to the aggregating characteristics of the active ingredients, are more likely to occur.

Furthermore, the time (Tmax) required for the drug to reach a maximum concentration in plasma is about 1 hour for both sitagliptin and dapagliflozin (1 to 4 hours for sitagliptin and 1 to 2 hours for dapagliflozin), and there is a need to develop a composite formulation including the two ingredients and at the same time having an excellent dissolution rate.

For the development of a composite formulation that may satisfy all pharmaceutical requirements such as proper productivity, dissolution rate, and stability, it is one of the most important and difficult problems in the field of composite formulation development to select an excipient that may satisfy the formulation compatibility for two different components.

PRIOR ART DOCUMENT

[Patent Document] KR 10-2016-0111237

DESCRIPTION OF EMBODIMENTS

Technical Problem

According to an aspect, provided is a composite formulation including sitagliptin or a pharmaceutically acceptable salt thereof, or a hydrate thereof, and dapagliflozin or a pharmaceutically acceptable salt thereof, or a hydrate thereof, each having excellent productivity, dissolution rate, stability, and compounding compatibility.

According to another aspect, provided is a method of preparing the composite formulation.

Other objects and advantages of the present application will become more apparent from the following detailed description in conjunction with the appended claims. Contents not described in this specification can be sufficiently recognized and inferred by a person skilled in the art within the technical field of the present application or a similar technical field, and thus description thereof is omitted.

Solution to Problem

According to an aspect, provided is a composite formulation including dry granules including sitagliptin or a pharmaceutically acceptable salt thereof, or a hydrate thereof, dapagliflozin or a pharmaceutically acceptable salt thereof, or a hydrate thereof, and sodium stearyl fumarate as a lubricant, wherein the dry granules may contain 1 wt % to 5 wt % of sodium stearyl fumarate based on the total weight of the composite formulation.

According to another aspect, provided is a method of preparing the composite formulation according to the one aspect, the method including preparing a mixture portion including sitagliptin or a pharmaceutically acceptable salt thereof, or a hydrate thereof, and dapagliflozin or a pharmaceutically acceptable salt thereof, or a hydrate thereof, an excipient, and a lubricant, dry-granulating the mixture portion, and further adding a lubricant to the granulated material and mixing together.

Advantageous Effects of Disclosure

The composite formulation including sitagliptin and dapagliflozin according to an aspect may prepare a composite formulation with excellent productivity, dissolution rate, stability, and compounding compatibility, thereby increasing drug compliance of patients need to be administered the two drugs together. The method of preparing the composite formulation according to an aspect may improve pharmaceutical properties of the composite formulation such as flowability and tableting properties, thereby enhancing manufacturing productivity.

BRIEF DESCRIPTION OF DRAWINGS

FIG. 1 illustrates images of pressed flakes and tablets according to the presence or absence of magnesium stearate.

FIG. 2 shows images of a tablet prepared by mixing and tableting sitagliptin and lactose, and a tablet prepared by mixing and tableting sitagliptin and an excipient other than lactose.

FIG. 3 shows images showing the appearances of the tablets of Example 5 and Comparative Example 5 after tableting, prepared with a different amount of sodium stearyl fumarate (PRUV®), and the results of measuring the time required for discharging mixed powder during preparation of each tablet.

FIG. 10 shows images of appearances of the tablets, results of measurement of thicknesses of the tablets, and calculated expansion rates of the tablets in Examples 9 to 11 and Comparative Examples 9 to 11, after storage for 1 week under accelerated exposure conditions (40° C. and 75% relative humidity in an open dish).

MODE OF DISCLOSURE

Figure 4:
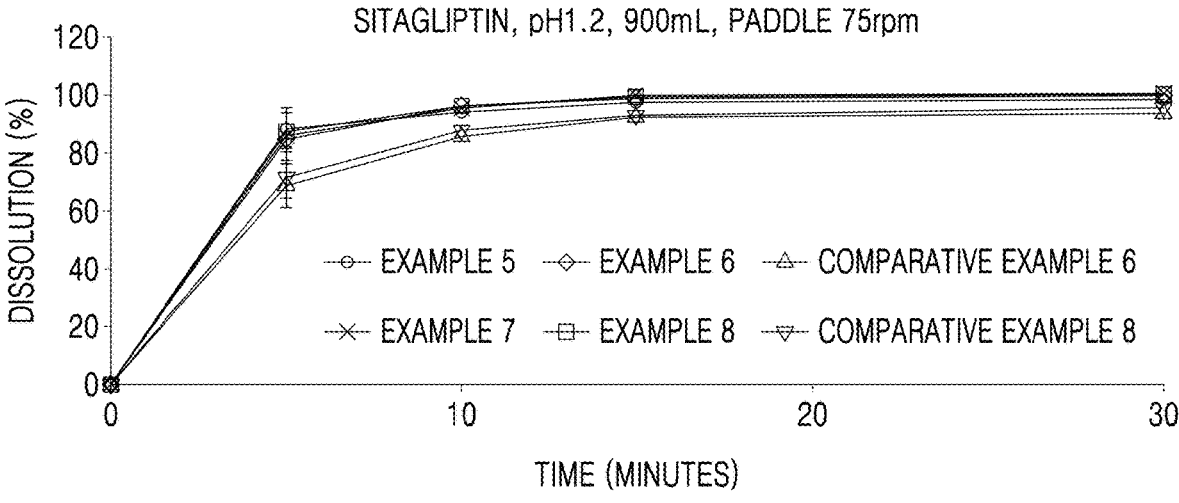
FIG. 4 is a graph showing the results of sitagliptin dissolution tests of Examples 5 to 8 and Comparative Examples 6 and 8.

Hereinafter, the present disclosure will be described in more detail.

All technical terms used herein have the same meaning as commonly understood by one of ordinary skill in the art, unless defined otherwise. In addition, although preferred methods or samples are described herein, similar or equivalent ones also fall within the scope of the present specification. In addition, the numerical values described herein are considered to include the meaning of "about" even if not specified. The contents of all publications incorporated herein by reference are hereby incorporated by reference in their entirety. As used herein, the term "about" means that the referenced value may vary to some extent. For example, "about 5" is meant to include any value between 4.5 and 5.5, between 4.75 and 5.25, or between 4.9 and 5.1, or between 4.95 and 5.05. As used herein, the terms "has", "may have", "comprises", or "may include" indicate the presence of a corresponding feature (e.g., a numerical value or a component such as an ingredient), and does not exclude the presence of additional features.

According to an aspect, provided is a composite formulation including: dry granules including sitagliptin or a pharmaceutically acceptable salt thereof, or a hydrate thereof;

dapagliflozin or a pharmaceutically acceptable salt thereof, or a hydrate thereof; and sodium stearyl fumarate as a lubricant, wherein the dry granules may contain 1 wt % to 5 wt % of sodium stearyl fumarate based on the total weight of the composite formulation.

In an embodiment, sodium stearyl fumarate may be additionally included as a lubricant on the outside of the dry granules, wherein a total amount of sodium stearyl fumarate present in the composite formulation may be 3 wt % to 8 wt % based on the total weight of the composite formulation.

The active ingredient sitagliptin or dapagliflozin may include all of the crystalline forms, hydrates, co-crystals, solvates, salts, diastereomers, or enantiomers thereof.

The pharmaceutically acceptable salt thereof refers to any pharmaceutically acceptable salt that may be commonly used in the art.

In one embodiment, the sitagliptin or a pharmaceutically acceptable salt thereof, or a hydrate thereof, may be sitagliptin phosphate hydrate.

In one embodiment, the dapagliflozin or a pharmaceutically acceptable salt thereof, or a hydrate thereof may be a pharmaceutically acceptable co-crystal of dapagliflozin. In one embodiment, the dapagliflozin or a pharmaceutically acceptable salt thereof may be dapagliflozin L-proline or dapagliflozin propanediol.

In one embodiment, the sitagliptin or a pharmaceutically acceptable salt thereof, or a hydrate thereof may be included in an amount of 10 wt % to 40 wt %, for example, 25 wt % to 35 wt % of the total weight of the composite formulation.

In one embodiment, the dapagliflozin or a pharmaceutically acceptable salt thereof, or a hydrate thereof may be included in an amount of 2 wt % to 10 wt %, or for example, 2 wt % to 6 wt % of the total weight of the composite formulation.

According to experimental results, magnesium stearate, which is most commonly used as a lubricant, increases productivity and tableting properties of the composite formulation of the present application, but has been found to be very disadvantageous because it increases the related compounds of the active ingredients over time (Test Examples 1 and 3). In contrast, sodium stearyl fumarate may increase productivity and tableting properties, and may also form a composite formulation stable enough to satisfy the standard levels of related compounds (Test Example 3). The sodium stearyl fumarate may be included in the dry granules in an amount of 1 wt % to 5 wt % based on the total weight of the composite formulation, and when the content is smaller than this range, sufficient productivity may not be secured, and when the content is greater than this range, the dissolution rate and stability of the active ingredient may be reduced (see Test Examples 4, 5, 6, 7, and 8). Optionally, sodium stearyl fumarate may be additionally included on the outside of the dry granules, wherein the total amount of sodium stearyl fumarate present in the composite formulation including the same may be 3 wt % to 8 wt % based on the total weight of the composite formulation. When the content is smaller than this range, sufficient productivity may not be secured, and when the content is greater than this range, the dissolution rate and stability of the active ingredient may be reduced (see Test Example 4 and Test Example 8).

The composite formulation may include one or more excipients selected from a diluent, a disintegrant, a binder, a lubricant, and a release control agent.

The diluent may be selected from the group consisting of, for example, D-mannitol, pregelatinized starch, low-substituted hydroxypropyl cellulose (L-HPC), microcrystalline cellulose (MCC), sucrose, sorbitol, xylitol, glucose, and any mixtures thereof, but is not limited thereto.

In one embodiment, the diluent may be selected from the group consisting of D-mannitol, pregelatinized starch, low-substituted hydroxypropyl cellulose (L-HPC), microcrystalline cellulose, and any mixture thereof.

The disintegrant may be, for example, selected from the group consisting of crospovidone, cross-linked sodium carboxymethylcellulose (cross-linked CMC Na or croscarmellose sodium), corn starch, carboxymethyl cellulose calcium, sodium starch glycolate, low-substituted hydroxypropyl cellulose (L-HPC) and any mixture thereof, but is not limited thereto. In an embodiment, the disintegrant may be low-substituted hydroxypropyl cellulose (L-HPC).

The binder may be selected from the group consisting of, for example, sodium carboxymethyl cellulose, ethyl cellulose, hydroxyethyl cellulose, hydroxypropyl cellulose, hydroxypropylmethyl cellulose, methyl cellulose, gelatin, povidone, and any mixtures thereof, but is not limited thereto. In one embodiment, the binder may be hydroxypropyl cellulose.

The release control agent may be selected from the group consisting of, for example, hydroxypropylmethyl cellulose, hydroxypropyl cellulose, carboxyvinyl polymer, polyvinyl alcohol, xanthan gum, guar gum, carboxymethyl cellulose and its derivatives, methyl cellulose and its derivatives, povidone-polyvinyl acetate copolymer, and any mixtures thereof, but is not limited thereto. In one embodiment, the release control agent may be hydroxypropyl cellulose.

In one embodiment, the composite formulation may include an excipient selected from microcrystalline cellulose (MCC), mannitol, pregelatinized starch, low-substituted hydroxypropyl cellulose (L-HPC), crospovidone, cross-linked carboxymethyl cellulose sodium (cross-linked CMC Na), hydroxypropyl cellulose (HPC), and any mixtures thereof.

In an embodiment, the dry granules may contain 5 wt % to 20 wt % of low-substituted hydroxypropyl cellulose (L-HPC) as a disintegrant based on the total weight of the composite formulation. When the content of L-HPC is smaller than the content range, a disintegration rate may be slowed, and accordingly, a problem may occur in that the initial dissolution rate is lowered. On the other hand, when the content of L-HPC is greater than the content range, the expansion rate of the tablet may rapidly increase due to water absorption during storage, resulting in significantly lower stability of properties (see Test Example 7) and a significant increase in related substances of the active ingredient (see Test Example 8).

In an embodiment, the dry granules may include water in an amount of 5 wt % or less based on the total weight of the composite formulation. When the water content is greater than this range, it was found that the water-sensitive related substances of the two active ingredients significantly increased (see Test Example 9). Therefore, when selecting batch/grade change raw material of an excipient, by selecting a raw material with a low water content, it is possible to prepare a stable composite formulation that may prevent an increase of related substances of the active ingredient.

The composite formulation may be in the form of a tablet, a capsule, or granules. In one embodiment, the composite formulation may be a mixed tablet or a double-layer tablet.

The composite formulation may include a pharmaceutically acceptable excipient additionally. The pharmaceutically acceptable excipient may be an ingredient selected from the group consisting of antioxidants, sweeteners, preservatives, coating agents, viscosity control agents, and any mixtures thereof.

The tablet may additionally be coated according to a method in the related art with a pharmaceutical immediate-release film coating base that may be generally used in the art. In one embodiment, the tablet may be coated with about 3% moisture-proof film with Opadry II coating solution based on the total weight of the uncoated tablet.

The composite formulation may be in a form in which the width and length are each about 5 mm to 15 mm. The composite formulation may have a thickness of about 3 mm to about 8 mm. In one embodiment, the composite formulation may be in a form in which the width and length are each about 5 mm to about 15 mm and the thickness is about 3 mm to about 8 mm. In one embodiment, the composite formulation may be in a form in which the width is about 10 mm to about 15 mm, the length is about 5 mm to about 10 mm, and the thickness is about 3 mm to about 8 mm. The width of the composite formulation may be, for example, about 10, 11, 12, 13, 14, or 15 mm. The length of the composite formulation may be, for example, about 5, 6, 7, 8, 9, or 10 mm. The thickness of the composite formulation may be, for example, about 3, 4, 5, 6, 7, or 8 mm.

The composite formulation may be a rectangular oval tablet. The composite formulation may be easier to swallow than when taking two individual tablets each containing an active ingredient. In general, when a tablet passes through the narrow area of the throat of the human body after the administration of the drug, the tablet passes through the throat while maintaining the smallest cross-sectional area. At this time, to maintain the small cross-sectional area of the tablet, throat swallowing takes place while maintaining the two smallest variables of the width, length, and thickness of the tablet. In the composite formulation including the two active ingredients of sitagliptin and dapagliflozin, according to one embodiment, the size and weight of the drug and the cross-sectional area upon swallowing may be reduced, and the convenience of medication for patients who feel uncomfortable when swallowing may be increased, compared to a case of simultaneously taking 2 individual tablets of single ingredients.

The composite formulation may further include one or more antidiabetic agents. For example, the composite formulation may include metformin or a pharmaceutically acceptable salt thereof. In one embodiment, the composite formulation may be a three-drug composite preparation including sitagliptin, dapagliflozin, and metformin.

Another aspect provides a method of preparing the composite formulation.

In one embodiment, the method of preparing the same may include:

preparing a mixture portion including sitagliptin or a pharmaceutically acceptable salt thereof, or a hydrate thereof, and dapagliflozin or a pharmaceutically acceptable salt thereof, or a hydrate thereof, an excipient, and a lubricant;

dry-granulating the mixture portion; and further adding a lubricant to the granulated material and mixing together.

The dry-granulating may be performed by a dry granulation method commonly used in the pharmaceutical field. In an embodiment, the dry granulation method may include forming compacted flakes by using a roller compactor.

In one embodiment, the preparation method may further include tableting granules mixed with a lubricant.

One or more embodiments of the disclosure will now be described in detail with reference to the following examples. However, these examples are only for illustrative purposes and are not intended to limit the scope of the one or more embodiments of the disclosure.

Test Methods

In the following Test Examples, related compound analysis, dissolution material analysis, and content analysis conditions were carried out in the following manners.

1. Related Compound Analysis Conditions [HPLC Method]

| Detector | Ultraviolet absorption spectrometer (measurement wavelength: 220 nm) |
| Column | C18 HPLC (15 cm × 4.6 mm, 2.7 μm) or an equivalent column |

8

-continued

| Column temperature | 30° C. | | | |
|---|---|---|---|---|
| | Time (mins) | Mobile phase A | Mobile phase B | Flux |
| Flux | 0 | 80 | 20 | 0.8 mL/min |
| | 5 | 80 | 20 | 0.8 mL/min |
| | 60 | 40 | 60 | 0.8 mL/min |
| | 65 | 80 | 20 | 0.8 mL/min |
| | 80 | 80 | 20 | 0.8 mL/min |
| Mobile phase | - Mobile phase A: pH 3.0 buffer solution/- Mobile phase B: acetonitrile | | | |
| Diluent | Mobile phase A solution:Mobile phase B solution = 60:40 (v/v) | | | |
| Analysis time | 80 minutes | | | |
| Injection volume | 10 μL of sample solution and standard solution | | | |
| Preparation of sample solution | About 20 tablets were precisely weighed. Then, the tablets were put in a 500 mL-volumetric flask, followed by adding a magnetic bar and about 600 mL of a diluent and stirring for 60 minutes to fully dissolve. Then, the magnetic bar was taken out, and the diluent was added up to the mark. This solution was filtered through a 0.45 μm-membrane filter and used as a sample solution. | | | |

2. Dissolution Analysis Conditions [HPLC Method]

| Detector | Ultraviolet absorption spectrometer (measurement wavelength: 205 nm) |
|---|---|
| Column | C18 HPLC (15 cm × 4.6 mm, 5 μm) or an equivalent column |
| Column temperature | 25° C. |
| Flux | 1.0 mL/min |
| Mobile phase | pH 7.2 buffer solution:acetonitrile = 3:2 (v/v) |
| Diluent | Identical to mobile phase |
| Analysis time | 30 minutes |
| Injection volume | 20 μL of sample solution and standard solution |
| Preparation of sample solution | After initiation of elution, at the sampling point to be analyzed, 10 mL of the eluate was taken, followed by filtering through a 0.45 μm membrane filter, as the sample solution. |
| Dissolution apparatus | Method 2 (paddle method) of dissolution test method of Korean Pharmacopoeia general test method |
| Dissolution test liquid | pH 1.2 liquid (first solution of disintegration test method of Korean Pharmacopoeia) 900 mL |
| Temperature of dissolution apparatus | 37° C. ± 0.5° C. |
| Rotation number of dissolution apparatus | 75 ± 2 rpm |
| Preparation of sample solution | 1 tablet of the drug was taken, and 900 mL of the dissolution test solution was used to perform test according to the dissolution conditions. 10 mL of the eluate was taken at a predetermined time interval, followed by filtering through a 0.45 μm membrane filter, to use as a sample solution. |

According to FDA Clinical Pharmacology Biopharmaceutics Review, the plasma peak time (Tmax) of sitagliptin and dapagliflozin are respectively about 1 to 4 hours and about 0.5 to 1.5 hours, and the bioavailability of sitagliptin and dapagliflozin are respectively 78% and 87%. Accordingly, a pH 1.2 dissolution test solution was selected as an IVIVC (in vitro-in vivo correlation) dissolution test solution of each active ingredient, and the dissolution sampling intervals were set at 5, 10, 15, 30, 45 minutes, and then the final saturation dissolution rate was measured.

9

3. Content Analysis Conditions [HPLC Method]

| | |
|---|---|
| Detector | Ultraviolet absorption spectrometer (measurement wavelength: 205 nm) |
| Column | C18 HPLC (15 cm × 4.6 mm, 5 μm) or an equivalent column |
| Column temperature | 25° C. |
| Flux | 1.0 mL/min |
| Mobile phase | pH 7.2 buffer solution:acetonitrile = 3:2 (v/v) |
| Diluent | Identical to mobile phase |
| Analysis time | 30 minutes |
| Injection volume | 20 μL of sample solution and standard solution |
| Preparation of sample solution | 5 T of tablets were taken to put them in a 500 mL-volumetric flask. Then, the flask was filled with about 300 mL of a diluent, and ultrasonic extraction was performed for about 1 hour. After cooling the volumetric flask at room temperature, the diluent was added up to the mark. 4 mL of the liquid in the volumetric flask was taken to put the liquid in a 50 mL-volumetric flask, and the diluent was added up to the mark. This solution was filtered through a 0.45 μm-membrane filter and used as a sample solution. |

Test Example 1: Related Compound Test According to Lubricants

Figure 1:
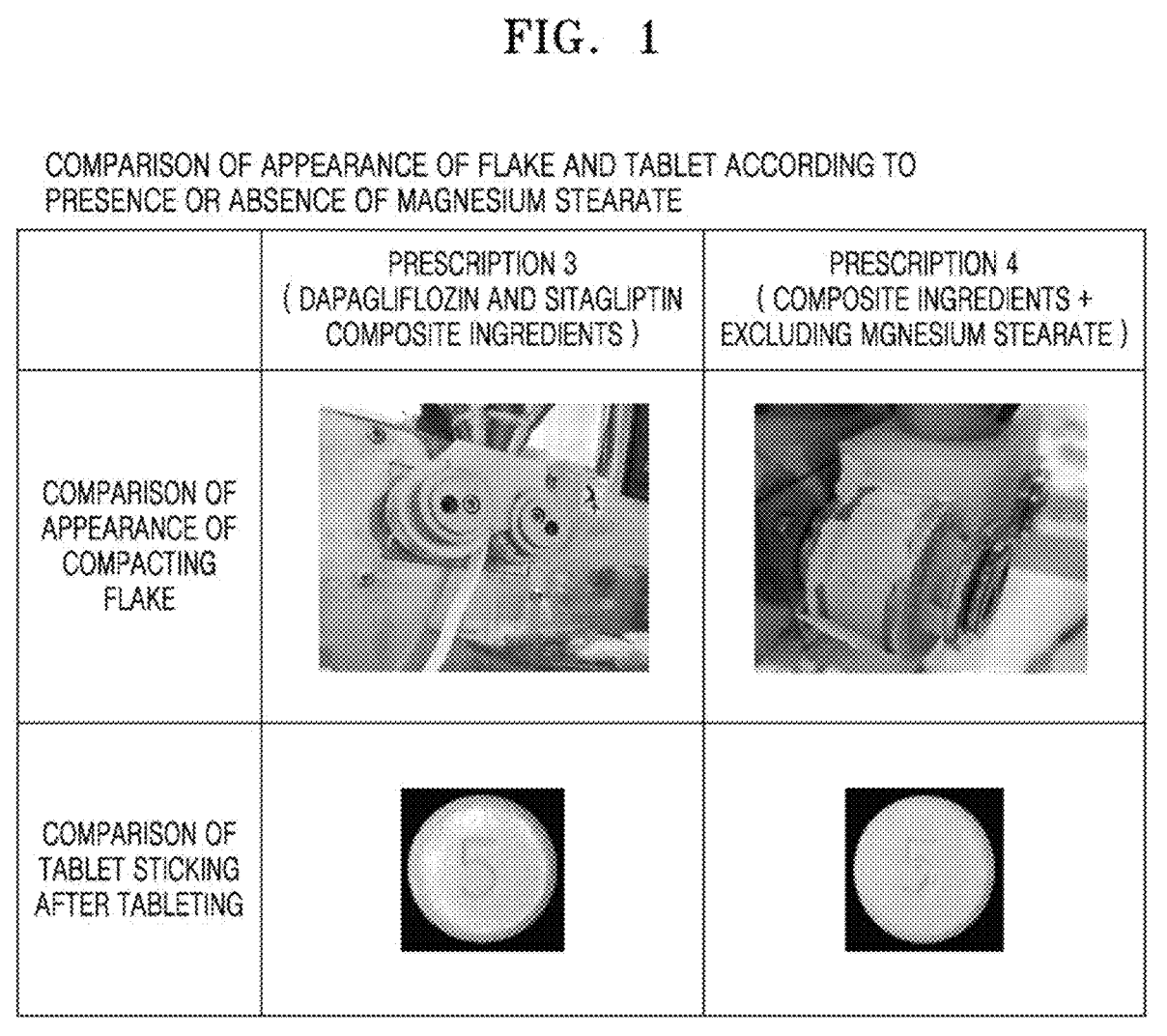

The stability of the composite formulation when commonly used magnesium stearate was used as a lubricant was tested. With prescriptions according to Table 1, tablets were prepared according to the following [Sample preparation method]. Then, related compounds were measured for each sample (Tables 1 to 3), the appearances of pressed flakes and tablets according to the presence or absence of magnesium stearate were compared (FIG. 1). FIG. 1 illustrates images of pressed flakes and tablets according to the presence or absence of magnesium stearate.

[Sample Preparation Method]

(1) Weighing: Each ingredient was weighed to be an amount of 1000 T.

(2) Sieving: All ingredients, except for a lubricant to be added in final mixing, were sieved through a 30-mesh sieve.

(3) Mixing: Powder having passed through the sieve was mixed with a Bin mixer at 17 rpm for 30 min.

(4) Compacting: Pressed flakes were formed using a roller compactor at a roll rpm of 3.0 and a screw rpm of 35.0 at a hydraulic pressure of 2.5 Mpa.

(5) Sizing: The flakes prepared in step (4) were sized with a 20-mesh using Oscillator.

(6) Final mixing: The resulting product prepared in step (5) and the remaining final mixing lubricant were added and mixed with a bin mixer at 17 rpm for 5 min.

(7) Tableting: Tableting was performed with a tablet hardness of 10 kp to 12 kp using an AutoTab-200TR (Ichihachi Seiki Co., Ltd, Japan) with a circular punch having a diameter of 8.0 mm.

TABLE 1

| Process | Component | Prescription 1 (Sitagliptin single ingredient) | Prescription 2 (Dapagliflozin single ingredient) | Prescription 3 (Composite ingredients of dapagliflozin and sitagliptin) | Prescription 4 (Composite ingredients excluding Mg Stearate) |
|---|---|---|---|---|---|
| Weighing ↓ Sieving and mixing ↓ | Sitagliptin phosphate hydrate | 128.5 | — | 128.5 | |
| Compacting ↓ Sizing | Dapagliflozin propanediol | — | 12.3 | 12.3 | |
| Final mixing | Microcrystalline cellulose (MCC) | 153.2 | 269.4 | 140.9. | 148.9 |
| | D-mannitol | | | 102.0 | |
| | Croscarmellose sodium | | | 8.3 | |
| | Magnesium stearate | | 4.0 | | 0.0 |
| | Magnesium stearate | | 4.0 | | 0.0 |
| Total (mg) | | | 400.0 | | 400.0 |

TABLE 2

Results of related compound under accelerated conditions
The results of total related compound (%) of sitagliptin [based
on the total related compound of 0.2% or less]

| | Prescription 1 (Sitagliptin single ingredient) | Prescription 2 (Dapagliflozin single ingredient) | Prescription 3 (Composite ingredients of dapagliflozin and sitagliptin) | Prescription 4 (Composite ingredients excluding Mg Stearate) |
|---|---|---|---|---|
| Initial state | 0.01 | — | 0.01 | 0.01 |
| 1 month under accelerated conditions | 0.03 | — | 0.09 | 0.04 |
| 3 months under accelerated conditions | 0.08 | — | 0.25 | 0.09 |

TABLE 3

Results of related compound under accelerated conditions
The results of total related compound (%) of dapagliflozin [based
on the total related compound of 2.0% or less]

| | Prescription 1 (Sitagliptin single ingredient) | Prescription 2 (Dapagliflozin single ingredient) | Prescription 3 (Composite ingredients of dapagliflozin and sitagliptin) | Prescription 4 (Composite ingredients + excluding Mg Stearate) |
|---|---|---|---|---|
| Initial state | — | 0.03 | 0.05 | 0.04 |
| 1 month under accelerated conditions | — | 0.20 | 0.78 | 0.22 |
| 3 months under accelerated conditions | — | 0.58 | 2.21 | 0.63 |

According to the above experimental results, when magnesium stearate was used as a lubricant in the mixed granules including sitagliptin and dapagliflozin together, related compounds were greatly increased under accelerated storage conditions. In addition, when magnesium stearate was excluded, there was a decrease in productivity, due to the issue of adhering to the punch and production equipment during the granulation process and product tableting. Therefore, it was confirmed that, though a lubricant is necessary for productivity and tableting properties, magnesium stearate lowers the stability of the active ingredients and is not appropriate.

Test Example 2: Related Compound Test According to Excipients

Preparation Example 1

To evaluate stability when the two active ingredients of sitagliptin and dapagliflozin coexist, tablets including 128.5 mg of sitagliptin phosphate hydrate (100 mg of sitagliptin) and 12.3 mg of dapagliflozin propanediol (10 mg of dapagliflozin) were prepared through compacting. Using an AutoTab-200TR (Ichihachi Seiki Co., Ltd, Japan) tableting apparatus, flakes were formed, and the amounts of related compounds generated under accelerated conditions (40° C./75% RH) for 1 month/2 months were measured to confirm stability.

Preparation Example 2

To find out the compounding compatibility of the active ingredient sitagliptin with excipients, sitagliptin was mixed with different types of excipients. The active ingredient sitagliptin and each excipient were sieved through a 20-mesh sieve, and then mixed with a Tubular mixer for 30 minutes. Then, the other active ingredient dapagliflozin was added thereto, mixed, and compacted to form tablets. Using an AutoTab-200TR (Ichihachi Seiki Co., Ltd, Japan) tableting apparatus, flakes were formed, and the amounts of related compounds generated under accelerated conditions (40° C./75% RH) for 1 month/2 months were measured to confirm stability.

Preparation Example 3

To find out the compounding compatibility of the active ingredient dapagliflozin with excipients, dapagliflozin was mixed with each different type of excipient. The active ingredient dapagliflozin and each excipient were sieved through a 20-mesh sieve, and then mixed with a Tubular mixer for 30 minutes. Then, the other active ingredient sitagliptin was added thereto, mixed, and compacted to form tablets. Using an AutoTab-200TR (Ichihachi Seiki Co., Ltd, Japan) tableting apparatus, flakes were formed, and the amounts of related compounds generated under accelerated conditions (40° C./75% RH) for 1 month/2 months were measured to confirm stability.

Standard Level for Total Related Compound Content

According to the permitted related compound standards in Korea, currently applied standard levels for total related compound content are 0.2% or less of total related compounds for sitagliptin, and less than 2.0% of total related compounds for dapagliflozin.

TABLE 4

Content of total related compound content of sitagliptin (%)

| | | Compounding compatibility of sitagliptin | | | | | | | | |
|---|---|---|---|---|---|---|---|---|---|---|
| Component | API + API | API + excipient (mg) | | | | | | | | |
| Sitagliptin phosphate hydrate | 128.5 mg | 128.5 mg (100 mg as sitagliptin) | | | | | | | | |
| Dapagliflozin propanediol | 12.3 mg | 12.3 mg (10 mg as dapagliflozin) | | | | | | | | |
| Excipient | — Dapagliflozin | 150 mg MCC | 150 mg DCP hydrate | 150 mg Lactose hydrate | 150 mg Mannitol | 150 mg DCP hydrate | 150 mg Pregelatinized starch | 150 mg L-HPC | 50 mg Crosspovidone | 50 mg C. CMC Na |
| Initial state | 0.01 | 0.01 | 0.01 | 0.01 | 0.01 | 0.02 | 0.01 | 0.01 | 0.02 | 0.01 |
| 1 month under accelerated conditions | 0.02 | 0.02 | 0.02 | 0.14 | 0.03 | 0.17 | 0.05 | 0.02 | 0.04 | 0.02 |
| 2 months under accelerated conditions | 0.03 | 0.03 | 0.03 | 0.28 | 0.04 | 0.31 | 0.07 | 0.06 | 0.05 | 0.03 |

The results of the related compound test performed using the tablets prepared in Preparation Example 1 and Preparation Example 2 are shown in Table 4. As shown in Table 4, for sitagliptin, when lactose hydrate or dicalcium phosphate (DCP) hydrate was included as an excipient, the total related compound content was greater than 0.2% for each case, failing to satisfy the standard level.

Specifically, when sitagliptin and lactose hydrate were mixed, and the appearance was observed after two months of acceleration, a browning phenomenon occurred due to the Maillard reaction that produces a brown substance at high temperature, confirming that the formulation is not suitable for prescription (FIG. 2). FIG. 2 shows images of a tablet prepared by mixing and tableting sitagliptin and lactose hydrate, and a tablet prepared by mixing and tableting sitagliptin and an excipient other than lactose.

TABLE 5

Compounding compatibility of dapagliflozin

| | | Compounding compatibility of sitagliptin | | | | | | | | |
|---|---|---|---|---|---|---|---|---|---|---|
| Component | API + API (mg) | API + excipient (mg) | | | | | | | | |
| Dapagliflozin propanediol | 12.3 | 12.3 mg (10 mg as dapagliflozin) | | | | | | | | |
| Sitagliptin phosphate hydrate | 128.5 mg | 128.5 mg (100 mg as sitagliptin) | | | | | | | | |
| Excipient | — Sitagliptin | 150 mg MCC | 150 mg DCP hydrate | 150 mg Lactose hydrate | 150 mg Mannitol | 150 mg DCP hydrate | 150 mg Pregelatinized starch | 150 mg L-HPC | 50 mg Crosspovidone | 50 mg C. CMC Na |

TABLE 5-continued

| Compounding compatibility of dapagliflozin | | | | | | | | | |
|---|---|---|---|---|---|---|---|---|---|
| Compounding compatibility of sitagliptin | | | | | | | | | |
| Initial state | 0.01 | 0.03 | 0.05 | 0.04 | 0.04 | 0.05 | 0.05 | 0.04 | 0.04 | 0.04 |
| 1 month under accelerated conditions | 0.02 | 0.04 | 1.79 | 0.05 | 0.07 | 0.98 | 0.07 | 0.05 | 0.05 | 0.05 |
| 2 months under accelerated conditions | 0.03 | 0.05 | 3.52 | 0.06 | 0.08 | 1.25 | 0.09 | 0.08 | 0.06 | 0.06 |

The results of the related compound test performed using the tablets prepared in Preparation Example 1 and Preparation Example 3 are shown in Table 5. As shown in Table 5, for dapagliflozin, when dicalcium phosphate (DCP) anhydride was included as an excipient, the total related compound content was greater than 2.0%, failing to satisfy the standard level. In addition, when dicalcium phosphate (DCP) hydrate was included as an excipient, the total related compound content satisfied the standard level, but was higher compared to the other excipients.

Test Example 3: Related Compound Test According to Lubricants and Excipients

Based on the stability comparison results with respect to each prescription in Test Examples 1 and 2, it was confirmed that it is necessary to choose lubricants or excipients suitable for production and having ensured stability. Accordingly, a stability test was carried out with various types of lubricants and excipients. After completion of the production of tablets, the stability test was carried out under accelerated and stress conditions.

With prescriptions according to Table 6, tablets were prepared according to [Sample preparation method] as follows.

[Sample Preparation Method]
(1) Weighing: Each ingredient was weighed to be an amount of 1000 T.
(2) Sieving: All excipients, except for a lubricant to be added in final mixing, were sieved through a 30-mesh sieve.
(3) Mixing: Powder having passed through the sieve was mixed with a Bin mixer at 17 rpm for 30 min.
(4) Compacting: Pressed flakes were formed using a roller compactor at a roll rpm of 3.0 and a screw rpm of 35.0 at a hydraulic pressure of 2.5 Mpa.
(5) Sizing: The flakes prepared in step (4) were sized with a 20-mesh using oscillator.
(6) Final mixing: The resulting product prepared in step (5) and the remaining final mixing lubricant were added and mixed with a bin mixer at 17 rpm for 5 min.
(7) Tableting: Tableting was performed with a tablet hardness of 12 kp to 14 kp using an AutoTab-200TR (Ichihachi Seiki Co., Ltd, Japan) with a rectangular punch having a width of 12.8 mm and a length of 7.0 mm.

TABLE 6

| | | | | | | | Prescription according to type of excipient/lubricant [unit: mg] | | | |
|---|---|---|---|---|---|---|---|---|---|---|
| Process | No. | Component | Example 1 | Example 2 | Example 3 | Example 4 | Comparative Example 1 | Comparative Example 2 | Comparative Example 3 | Comparative Example 4 |
| Characteristic of prescription | | | Excipient: MCC Lubricant: PRUV® | Excipient: MCC + Manitol Lubricant: PRUV® | Excipient: MCC + L-HPC Lubricant: PRUV® | Excipient: MCC+ DCP Lubricant: PRUV® | Excipient: MCC + Manitol Lubricant: GMS | Excipient: MCC + Manitol Lubricant: Mg-Stearate | Excipient: MCC + Manitol Lubricant: Ca-Stearate | Excipient: MCC + Manitol Lubricant: Sucrose Stearate |
| Weighing ↓ | 1 | Sitagliptin phosphate hydrate | | | | | 128.5 | | | |
| Sieving and mixing ↓ | 2 | Dapagliflozin propanediol | | | | | 12.3 | | | |
| | 3 | Microcrystalline cellulose (MCC) | 242.9 | | | | 142.9 | | | |
| Compacting ↓ Sizing | 4 | D-mannitol | — | 100.0 | — | — | | | 100.0 | |
| | 5 | Low-substituted hydroxypropyl cellulose (L-HPC) | — | — | 100.0 | — | — | — | — | — |
| | 6 | Dicalcium phosphate anhydrous (DCP) | — | — | — | 100.0 | — | — | — | — |
| | 7 | Croscarmellose sodium | | | | | 8.3 | | | |
| | 8 | Sodium stearyl fumarate (PRUV®) | | 14.0 | | | — | — | — | — |

TABLE 6-continued

Prescription according to type of excipient/lubricant [unit: mg]

| Process | No. | Component | Example 1 | Example 2 | Example 3 | Example 4 | Comparative Example 1 | Comparative Example 2 | Comparative Example 3 | Comparative Example 4 |
|---------|-----|-----------|-----------|-----------|-----------|-----------|----------------------|----------------------|----------------------|----------------------|
| | 9 | Glyceryl monostearate (GMS) | — | — | — | — | 14.0 | — | — | |
| | 10 | Mg-Stearate | — | — | — | — | — | 14.0 | — | |
| | 11 | Ca-Stearate | — | — | — | — | — | — | 14.0 | |
| | 12 | Sucrose Stearate | — | — | — | — | — | — | — | 14.0 |
| Final mixing | 13 | Sodium stearyl fumarate (PRUV ®) | | | 14.0 | | — | — | — | — |
| | 14 | Glyceryl monostearate | — | — | — | — | 14.0 | — | — | — |
| | 15 | Mg-Stearate | — | — | — | — | — | 14.0 | — | — |
| | 16 | Ca-Stearate | — | — | — | — | — | — | 14.0 | — |
| | 17 | Sucrose Stearate | — | — | — | — | — | — | — | 14.0 |
| | | Total (mg) | | | | | 420.0 | | | |

The results of evaluation of the total related compounds of sitagliptin during storage under accelerated conditions (40° C., 75% relative humidity) are shown in Table 7.

TABLE 7

The results of total related compound (%) of sitagliptin
[based on the total related compound of 0.2% or less]

| | Example 1 | Example 2 | Example 3 | Example 4 | Comparative Example 1 | Comparative Example 2 | Comparative Example 3 | Comparative Example 4 |
|---|---|---|---|---|---|---|---|---|
| Initial state | 0.01 | 0.01 | 0.02 | 0.02 | 0.02 | 0.01 | 0.02 | 0.02 |
| 1 month under accelerated conditions | 0.02 | 0.03 | 0.03 | 0.04 | 0.22 | 0.26 | 0.22 | 0.24 |
| 3 months under accelerated conditions | 0.05 | 0.06 | 0.05 | 0.09 | 0.62 | 0.81 | 0.73 | 0.82 |

The results of evaluation of the total related compounds of dapagliflozin during storage under accelerated conditions (40° C., 75% relative humidity) are shown in Table 8.

TABLE 8

The results of total related compound (%) of dapagliflozin
[based on the total related compound of 2.0% or less]

| | Example 1 | Example 2 | Example 3 | Example 4 | Comparative Example 1 | Comparative Example 2 | Comparative Example 3 | Comparative Example 4 |
|---|---|---|---|---|---|---|---|---|
| Initial state | 0.04 | 0.05 | 0.05 | 0.05 | 0.05 | 0.05 | 0.05 | 0.05 |
| 1 month under accelerated conditions | 0.23 | 0.22 | 0.26 | 0.92 | 0.42 | 0.53 | 0.48 | 0.58 |

TABLE 8-continued

The results of total related compound (%) of dapagliflozin
[based on the total related compound of 2.0% or less]

| | Example 1 | Example 2 | Example 3 | Example 4 | Comparative Example 1 | Comparative Example 2 | Comparative Example 3 | Comparative Example 4 |
|---|---|---|---|---|---|---|---|---|
| 3 months under accelerated conditions | 0.68 | 0.73 | 0.75 | 2.30 | 1.62 | 1.89 | 1.79 | 1.97 |

The results of evaluation of the total related compound of sitagliptin during storage under stress conditions (60° C.) are shown in Table 9.

TABLE 9

The results of total related compound (%) of sitagliptin
[based on the total related compound of 0.2% or less]

| | Example 1 | Example 2 | Example 3 | Example 4 | Comparative Example 1 | Comparative Example 2 | Comparative Example 3 | Comparative Example 4 |
|---|---|---|---|---|---|---|---|---|
| Initial state | 0.02 | 0.01 | 0.01 | 0.02 | 0.02 | 0.01 | 0.02 | 0.02 |
| 1 month under stress conditions | 0.11 | 0.12 | 0.13 | 0.14 | 0.28 | 0.38 | 0.33 | 0.35 |
| 3 months under stress conditions | 0.14 | 0.16 | 0.18 | 0.18 | 0.85 | 1.18 | 1.02 | 1.21 |

The results of evaluation of the total related compounds of dapagliflozin during storage under stress conditions (60° C.) are shown in Table 10.

TABLE 10

The results of total related compound (%) of dapagliflozin
[based on the total related compound of 2.0% or less]

| | Example 1 | Example 2 | Example 3 | Example 4 | Comparative Example 1 | Comparative Example 2 | Comparative Example 3 | Comparative Example 4 |
|---|---|---|---|---|---|---|---|---|
| Initial state | 0.05 | 0.05 | 0.04 | 0.05 | 0.05 | 0.05 | 0.05 | 0.05 |
| 1 month under stress conditions | 0.24 | 0.26 | 0.33 | 1.11. | 0.51 | 0.60 | 0.54 | 0.66 |
| 3 months under stress conditions | 0.98 | 0.99 | 1.08 | 2.75 | 1.97 | 2.25 | 2.16 | 2.42 |

According to the results of Tables 7 to 10, when sodium stearyl fumarate (PRUV®) was used as the lubricant (Examples 1 to 3), the standard levels of related compounds were satisfied, indicating that sodium stearyl fumarate (PRUV®) is an appropriate lubricant that does not impair stability. However, according to Comparative Examples 1 to 4, it was confirmed that the other lubricants glyceryl monostearate, magnesium stearate, calcium stearate, and sucrose stearate did not meet the standard levels under the accelerated and stress conditions.

In addition, when microcrystalline cellulose, D-mannitol, and/or low-substituted hydroxypropyl cellulose were used as excipients, along with sodium stearyl fumarate (PRUV®), the stability of related compounds was ensured (Examples 1 to 3). However, when dicalcium phosphate anhydrous was used as excipient along with sodium stearyl fumarate (PRUV®) (Example 4), the standard level of related compounds of dapagliflozin under accelerated and stress conditions was not satisfied.

Test Example 4: Evaluation of Productivity According to Lubricant Amount

In Test Example 3, productivity according to the amount of lubricant was evaluated with sodium stearyl fumarate (PRUV®) and microcrystalline cellulose, D-mannitol, and low-substituted hydroxypropyl cellulose, of which stability was secured. In addition, after completion of sample preparation, stability evaluation was carried out under accelerated and stress conditions. The sample preparation was carried out according to the same method as in Test Example 3.

TABLE 11

Prescription according to content of lubricant [unit: mg]

| Process | No. | Excipient | Comparative Example 5 | Example 5 | Example 6 | Comparative Example 6 | Comparative Example 7 | Example 7 | Example 8 | Comparative Example 8 |
|---|---|---|---|---|---|---|---|---|---|---|
| Characteristic of prescription | | | Excipient: MCC + mannitol PRUV ® prescription according to quantity | | | | Excipient: MCC + L-HPC PRUV ® prescription according to quantity | | | |
| Weighing | 1 | Sitagliptin phosphate hydrate | | | | 128.5 | | | | |
| ↓ | 2 | Dapagliflozin propanediol | | | | 12.3 | | | | |
| Sieving and mixing | 3 | Microcrystalline cellulose (MCC) | 162.5 | 158.3 | 137.3 | 124.7 | 162.5 | 158.3 | 137.3 | 124.7 |
| | 4 | D-mannitol | | 100.0 | | | — | — | — | — |
| ↓ Compacting | 5 | Low-substituted hydroxypropyl cellulose (L-HPC) | — | — | — | — | | | 100.0 | |
| ↓ | 6 | Croscarmellose sodium | | | | 8.3 | | | | |
| Sizing | 7 | Sodium stearyl fumarate (PRUV ®) | 4.2 | 8.4 | 25.2 | 37.8 | 4.2 | 8.4 | 25.2 | 37.8 |
| Final mixing | 13 | Sodium stearyl fumarate (PRUV ®) | 4.2 | 4.2 | 8.4 | 8.4 | 4.2 | 4.2 | 8.4 | 8.4 |
| | | Total (mg) | | | | 420.0 | | | | |

21

The appearance of the tablets of Examples 5 and Comparative Example 5 after tableting were photographed, and the time required for discharging granules during tableting into each tablet was measured. The results are shown in FIG. 3. "The time required for discharging granules during tableting" above refers to the time it takes during tableting for all the granules filled in a feeder to be compressed into tablets and for all of the granules inside the feeder to be exhausted. This test was evaluated based on an amount of 420 g of granules filled in the feeder.

Test Example 5: Evaluation of Stability According to Lubricant Amount

For the samples prepared according to Table 11, the total related compounds of sitagliptin in tablets according to lubricant amount during storage under accelerated conditions (40° C. and 75% relative humidity) was evaluated. The results are shown in Table 12.

TABLE 12

Evaluation of related compound in relation to sodium stearyl fumarate (PRUV ®) quantity under accelerated conditions
The total related compound (%) of sitagliptin
[based on the total related compound of 0.2% or less]

| Sitagliptin | Comparative Example 5 | Example 5 | Example 6 | Comparative Example 6 | Comparative Example 7 | Example 7 | Example 8 | Comparative Example 8 |
|---|---|---|---|---|---|---|---|---|
| Initial state | 0.01 | 0.01 | 0.01 | 0.01 | 0.01 | 0.02 | 0.02 | 0.01 |
| 1 month under accelerated conditions | 0.02 | 0.02 | 0.03 | 0.02 | 0.02 | 0.02 | 0.03 | 0.02 |
| 3 months under accelerated conditions | 0.04 | 0.05 | 0.05 | 0.07 | 0.04 | 0.04 | 0.05 | 0.06 |

The results of evaluation of the total related compound of dapagliflozin in tablets according to lubricant amount during storage under accelerated conditions (40° C. and 75% relative humidity) are shown in Table 13.

TABLE 13

Evaluation of related compound in relation to sodium stearyl fumarate (PRUV ®) quantity under accelerated conditions
The total related compound (%) of dapagliflozin
[based on the total related compound of 2.0% or less]

| Dapagliflozin | Comparative Example 5 | Example 5 | Example 6 | Comparative Example 6 | Comparative Example 7 | Example 7 | Example 8 | Comparative Example 8 |
|---|---|---|---|---|---|---|---|---|
| Initial state | 0.05 | 0.04 | 0.05 | 0.04 | 0.04 | 0.03 | 0.05 | 0.05 |
| 1 month under accelerated conditions | 0.21 | 0.24 | 0.25 | 0.37 | 0.23 | 0.22 | 0.28 | 0.35 |

22

TABLE 13-continued

Evaluation of related compound in relation to sodium stearyl fumarate (PRUV ®) quantity under accelerated conditions
The total related compound (%) of dapagliflozin
[based on the total related compound of 2.0% or less]

| Dapagliflozin | Comparative Example 5 | Example 5 | Example 6 | Comparative Example 6 | Comparative Example 7 | Example 7 | Example 8 | Comparative Example 8 |
|---|---|---|---|---|---|---|---|---|
| 3 months under accelerated conditions | 0.41 | 0.58 | 0.75 | 0.88 | 0.45 | 0.55 | 0.80 | 0.82 |

The results of evaluation of the total related compound of sitagliptin in tablets according to lubricant amount during storage under stress conditions (60° C.) are shown in Table 14.

TABLE 14

Evaluation of related compound in relation to sodium stearyl fumarate (PRUV ®) quantity under stress conditions
The total related compound (%) of sitagliptin
[based on the total related compound of 0.2% or less]

| Sitagliptin | Comparative Example 5 | Example 5 | Example 6 | Comparative Example 6 | Comparative Example 7 | Example 7 | Example 8 | Comparative Example 8 |
|---|---|---|---|---|---|---|---|---|
| Initial state | 0.01 | 0.02 | 0.01 | 0.02 | 0.02 | 0.02 | 0.01 | 0.02 |
| 1 month under stress conditions | 0.04 | 0.07 | 0.06 | 0.09 | 0.03 | 0.06 | 0.07 | 0.08 |
| 3 months under stress conditions | 0.08 | 0.09 | 0.08 | 0.17 | 0.06 | 0.07 | 0.09 | 0.16 |

The results of evaluation of the total related compound of dapagliflozin in tablets according to lubricant amount during storage under stress conditions (60° C.) are shown in Table 14.

TABLE 15

Evaluation of related compound in relation to sodium stearyl fumarate (PRUV ®) quantity under stress conditions
The total related compound (%) of dapagliflozin
[based on the total related compound of 2.0% or less]

| Dapagliflozin | Comparative Example 5 | Example 5 | Example 6 | Comparative Example 6 | Comparative Example 7 | Example 7 | Example 8 | Comparative Example 8 |
|---|---|---|---|---|---|---|---|---|
| Initial state | 0.04 | 0.04 | 0.05 | 0.05 | 0.04 | 0.04 | 0.04 | 0.05 |
| 1 month under stress conditions | 0.14 | 0.24 | 0.28 | 0.62 | 0.17 | 0.23 | 0.31 | 0.57 |
| 3 months under stress conditions | 0.48 | 0.54 | 0.78 | 1.82 | 0.53 | 0.61 | 0.82 | 1.77 |

Test Example 6: Evaluation of Dissolution Rate
According to Lubricant Amount

Figure 5:
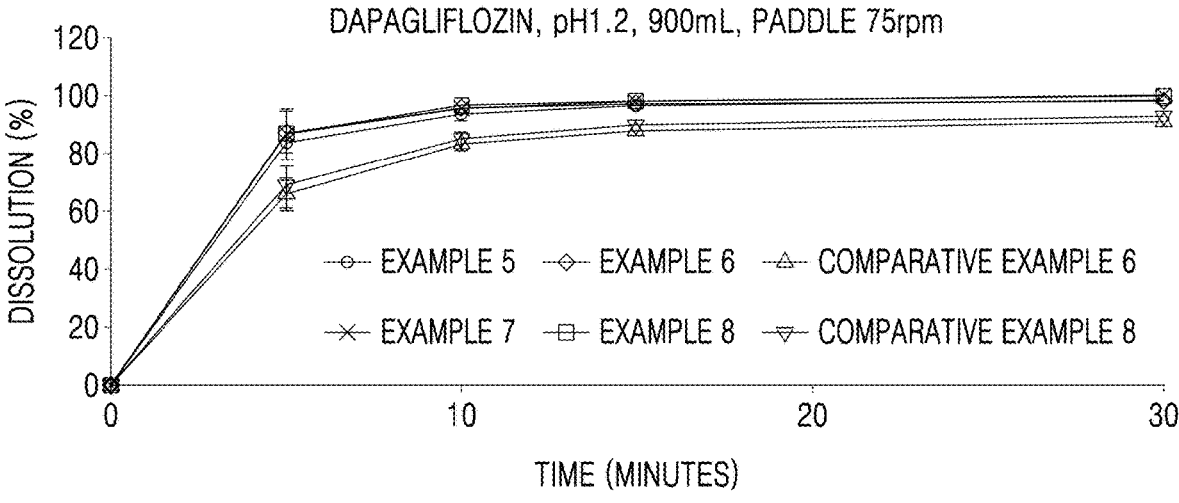
FIG. 5 is a graph showing the results of dapagliflozin dissolution tests of Examples to 8 and Comparative Examples 6 and 8.

For the samples prepared according to Table 11, dissolution rate evaluation was carried out, and the results are shown in FIGS. 4 and 5.

FIG. 4 is a graph showing the results of a sitagliptin dissolution test of Examples 5 to 8 and Comparative Examples 6 and 8.

FIG. 5 is a graph showing the results of a dapagliflozin dissolution test of Examples to 8 and Comparative Examples 6 and 8.

In addition, the amounts of the active ingredients of Examples 5-8 and Comparative Examples 6 and 8 were evaluated. The results are shown in Tables 16 and 17.

TABLE 16

| | The results of content of sitagliptin | | | | | |
|---|---|---|---|---|---|---|
| Content (n = 3) | Example 5 | Example 6 | Comparative Example 6 | Example 7 | Example 8 | Comparative Example 8 |
| Content ± standard deviation | 99.8 ± 0.4 | 101.2 ± 1.2 | 100.7 ± 0.7 | 99.6 ± 1.0 | 99.5 ± 1.8 | 101.7 ± 1.5 |

TABLE 17

| | The results of content of dapagliflozin | | | | | |
|---|---|---|---|---|---|---|
| Content (n = 3) | Example 5 | Example 6 | Comparative Example 6 | Example 7 | Example 8 | Comparative Example 8 |
| Content ± standard deviation | 99.9 ± 0.6 | 100.5 ± 0.8 | 100.2 ± 1.3 | 100.4 ± 1.4 | 101.4 ± 0.7 | 100.5 ± 1.5 |

According to the test result of Test Example 4, when the content of sodium stearyl fumarate did not reach 3% of the total weight of the tablet (Comparative Examples 5 and 7), the amount of lubricant was insufficient, resulting in tableting defects. In addition, it was confirmed that productivity was lowered because during the tableting process, the time required for discharging granules during tableting was delayed. However, when the content of sodium stearyl fumarate was 3% or more of the total weight of the tablet (Examples 5 to 8 and Comparative Examples 6 and 8), tableting into tablets was possible without tableting defects. Referring to FIG. 3, for Example 5, in which the content of sodium stearyl fumarate was 3% or more of the total weight of the tablet, it was possible to form tablets smoothly without tableting defects, with a significantly shorter time required for discharging mixture powder, compared to Comparative Example 5, in which the content of sodium stearyl fumarate was less than 3% of the total weight of the tablet.

According to the test results of Test Example 5, in Comparative Examples 5 to 8 and Examples 5 to 8, the stability of related substances which conformed to the standard level was ensured under accelerated and stress conditions. However, Comparative Example 6 and Comparative Example 8 having a relatively high lubricant ratio, showed a tendency for the related compounds of both sitagliptin and dapagliflozin to increase under stress conditions to the standard levels.

According to the test results of Test Example 6, it was confirmed that when sodium stearyl fumarate was present in more than 8% of the total weight of the tablet, the dissolution rate of the active ingredients was reduced. Specifically, in comparison of dissolution patterns, Comparative Examples 6 and 8 showed a decrease in dissolution rate, as compared with those of Examples 6 and 8 (see FIGS. 4 and 5). In addition, according to the content evaluation result of Test Example 8, it was confirmed that there was no decrease in the content of the active ingredients in each tablet (see Tables 16 and 17). Taken together, it was determined that the dissolution rate decreased due to the over-lubrication of the granules.

Test Example 7: Evaluation of Dissolution Rate,
Productivity, and Appearance Stability According to
Amount of Lubricant and Excipient Tablets containing sitagliptin and dapagliflozin as active ingredients were prepared according to the compositions shown in Tables 18 and 19.

Specifically, sitagliptin hydrochloride monohydrate, dapagliflozin propanediol, microcrystalline cellulose, D-mannitol, low-substituted hydroxypropyl cellulose, croscarmellose sodium, hydroxypropyl cellulose, and sodium stearyl fumarate were sieved through a 20-mesh sieve to crush large agglomerates, and mixed well. This mixture was formed into flakes using a roller compactor (TF-1-A60, Freund vector), and then sieved through a 20-mesh sieve to prepare dry granules. The final mixture portion was prepared by further mixing the prepared dry granules with sodium stearyl fumarate as a lubricant for 5 minutes. The prepared final mixture was tableted to a suitable hardness using a tablet press (Autotab-200TR, Ichihashi Seiki) to prepare a semi-finished product in an uncoated tablet state.

TABLE 18

| | Preparation of tablets of Examples 9 to 14 [unit: mg] | | | | | |
|---|---|---|---|---|---|---|
| | Component | Example 9 | Example 10 | Example 11 | Example 12 | Example 13 | Example 14 |
| Compacting | Sitagliptin phosphate monohydrate | 128.5 | 128.5 | 128.5 | 128.5 | 128.5 | 128.5 |
| | Dapagliflozin propanediol | 12.3 | 12.3 | 12.3 | 12.3 | 12.3 | 12.3 |
| | Microcrystalline cellulose (PH112) | 136.6 | 126.6 | 106.6 | 122.6 | 118.6 | 110.6 |
| | D-mannitol | 70.3 | 60.3 | 40.3 | 60.3 | 60.3 | 60.3 |
| | Low-substituted hydroxypropyl cellulose (LH-11) | 20.0 | 40.0 | 80.0 | 40.0 | 40.0 | 40.0 |
| | Croscarmellose sodium (Acdisol) | 8.3 | 8.3 | 8.3 | 8.3 | 8.3 | 8.3 |
| | Hydroxypropyl cellulose (EXF) | 12.0 | 12.0 | 12.0 | 12.0 | 12.0 | 12.0 |
| | Sodium stearyl fumarate | 4.0 | 4.0 | 4.0 | 8.0 | 12.0 | 20.0 |
| Final mixing | Sodium stearyl fumarate | 8.0 | 8.0 | 8.0 | 8.0 | 8.0 | 8.0 |
| | Uncoated tablet (total weight) | 400.0 | 400.0 | 400.0 | 400.0 | 400.0 | 400.0 |

TABLE 19

Preparation of tablets of Comparative Examples 9 to 14 [unit: mg]

| | Component | Example 9 | Example 10 | Example 11 | Example 12 | Example 13 | Example 14 |
|---|---|---|---|---|---|---|---|
| Com-pacting | Sitagliptin phosphate monohydrate | 128.5 | 128.5 | 128.5 | 128.5 | 128.5 | 128.5 |
| | Dapagliflozin propanediol | 12.3 | 12.3 | 12.3 | 12.3 | 12.3 | 12.3 |
| | Microcrystalline cellulose (PH112) | 146.6 | 141.6 | 86.6 | 130.6 | 102.6 | 98.6 |
| | D-mannitol | 80.3 | 75.3 | 20.3 | 60.3 | 60.3 | 60.3 |
| | Low-substituted hydroxypropyl cellulose (LH-11) | — | 10.0 | 120.0 | 40.0 | 40.0 | 40.0 |
| | Croscarmellose sodium (Acdisol) | 8.3 | 8.3 | 8.3 | 8.3 | 8.3 | 8.3 |
| | Hydroxypropyl cellulose (EXF) | 12.0 | 12.0 | 12.0 | 12.0 | 12.0 | 12.0 |
| | Sodium stearyl fumarate | 4.0 | 4.0 | 4.0 | — | 28.0 | 32.0 |
| Final mixing | Sodium stearyl fumarate | 8.0 | 8.0 | 8.0 | 8.0 | 8.0 | 8.0 |
| | Uncoated tablet (total weight) | 400.0 | 400.0 | 400.0 | 400.0 | 400.0 | 400.0 |

The dissolution rates of sitagliptin and dapagliflozin of Examples 9 to 14 and Comparative Examples 9 to 14 were measured, and the results are shown in FIGS. 6 to 9.

In addition, appearances of the tablets, results of measurement of thicknesses of the tablets, and calculated expansion rates of the tablets in Examples 9 to 11 and Comparative Examples 9 to 11 were evaluated, after storage for 1 week under accelerated exposure conditions (40° C. and 75% relative humidity in an open dish). The results thereof are shown in FIG. 10.

Figure 11:
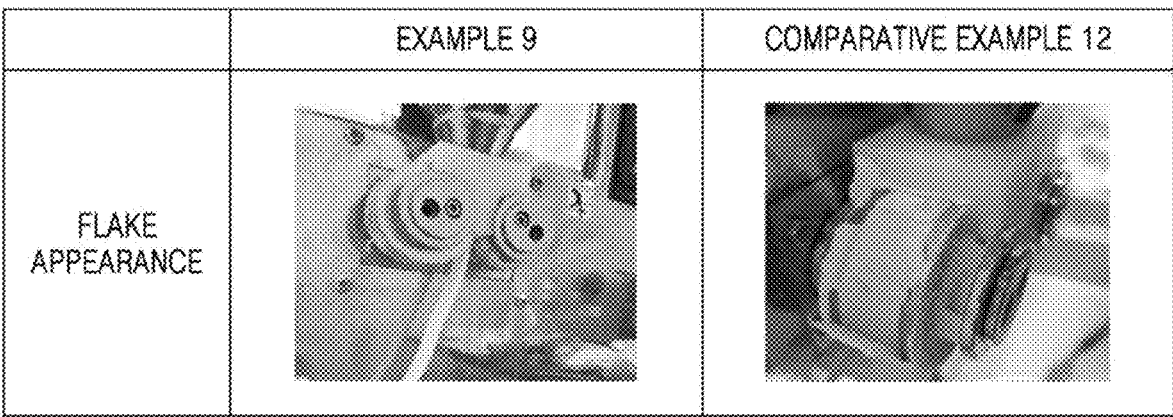
FIG. 11 shows images of appearances of flakes upon compacting for manufacture of dry granules according to the presence or absence of sodium stearyl fumarate (PRUV®) in Example 9 and Comparative Example 12.

In addition, the appearance of flakes during compacting for preparing the dry granules of Example 9 containing sodium stearyl fumarate in the granules and the dry granules of Comparative Example 12 without sodium stearyl fumarate in the granules were compared. Images of the appearances of the flakes are shown in FIG. 11.

[Comparison of Dissolution Pattern and Appearance Stability According to the Amount of L-HPC]

Figure 6:
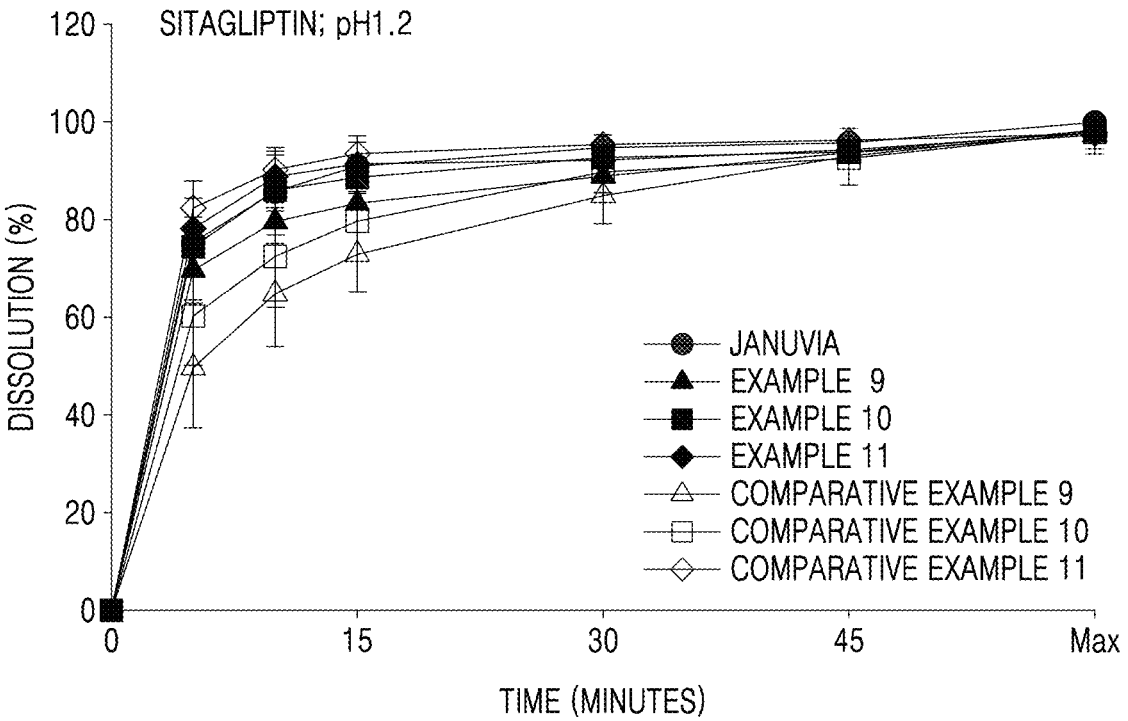
FIGS. 6 to 9 are each a graph showing the results of sitagliptin and dapagliflozin dissolution tests of Examples 9 to 14 and Comparative Examples 9 to 14, with a different amount of sodium stearyl fumarate (PRUV®) and/or L-HPC in the composite formulation.
Figure 7:
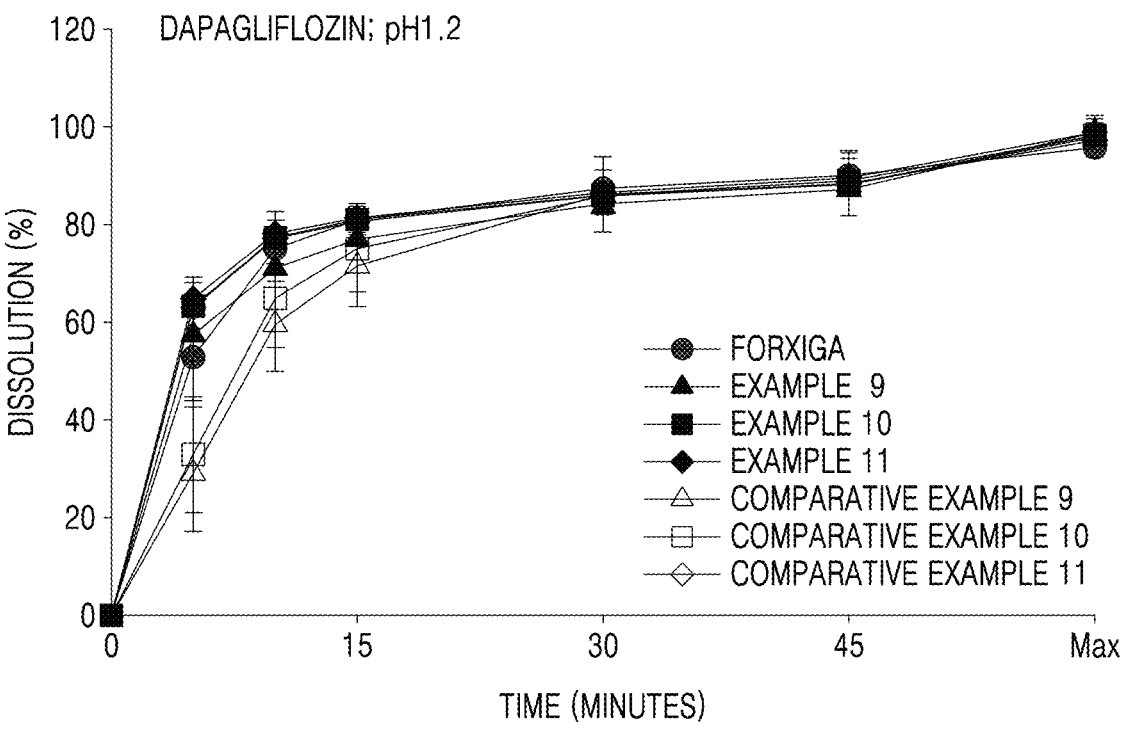

As shown in FIGS. 6 and 7, upon comparison of dissolution pattern of Examples 9 to 11 and Comparative Examples 9 to 11, in case of Examples 9 to 11, each active ingredient was similar with a reference drug, and this result is generally because L-HPC acts as a diluent and a disintegrant at the same time, and thus, the initial dissolution rate increases due to the increase in the initial disintegration power, and this leads to an increase in the initial dissolution rate, which appears to show a pattern similar to the dissolution of the reference drug. In Comparative Examples 9 and 10 with a relatively small amount of L-HPC, it was confirmed that the initial dissolution rate was low. This additionally causes a great dissolution rate deviation due to an increase in the amount of microcrystalline cellulose, a water-insoluble excipient with a relatively slow disintegration rate, which may be a problem for uniform drug administration to patients. In contrast, in Comparative Example 11, which had a relatively large amount of L-HPC, a fast initial dissolution rate and a similar pattern to that of the reference drug were observed, but it was confirmed that excessive use of a disintegrant may cause problems in appearance and accelerated stability thereafter. As shown in FIG. 10, in Comparative Example 11, which had 30 wt % of L-HPC, the expansion rate rapidly increased by water absorption, and it was confirmed that the appearance of the tablet greatly changed, which may cause a problem in appearance stability.

In conclusion, through dissolution evaluation, it was confirmed that the amount of L-HPC for securing initial disintegration power was effective in the range of 5 wt % or more relative to the total weight of the tablet, but there was a problem in appearance stability when L-HPC is excessively contained.

[Comparison of Dissolution Pattern and Productivity According to the Amount of PRUV]

Figure 8:
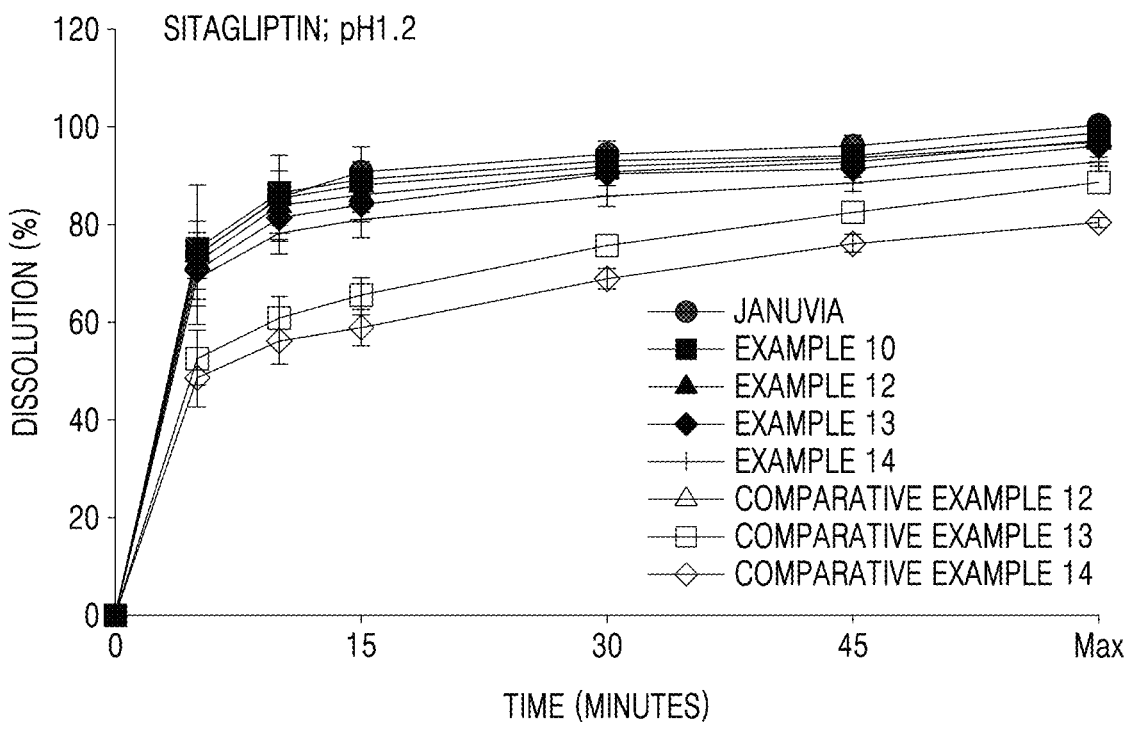
Figure 9:
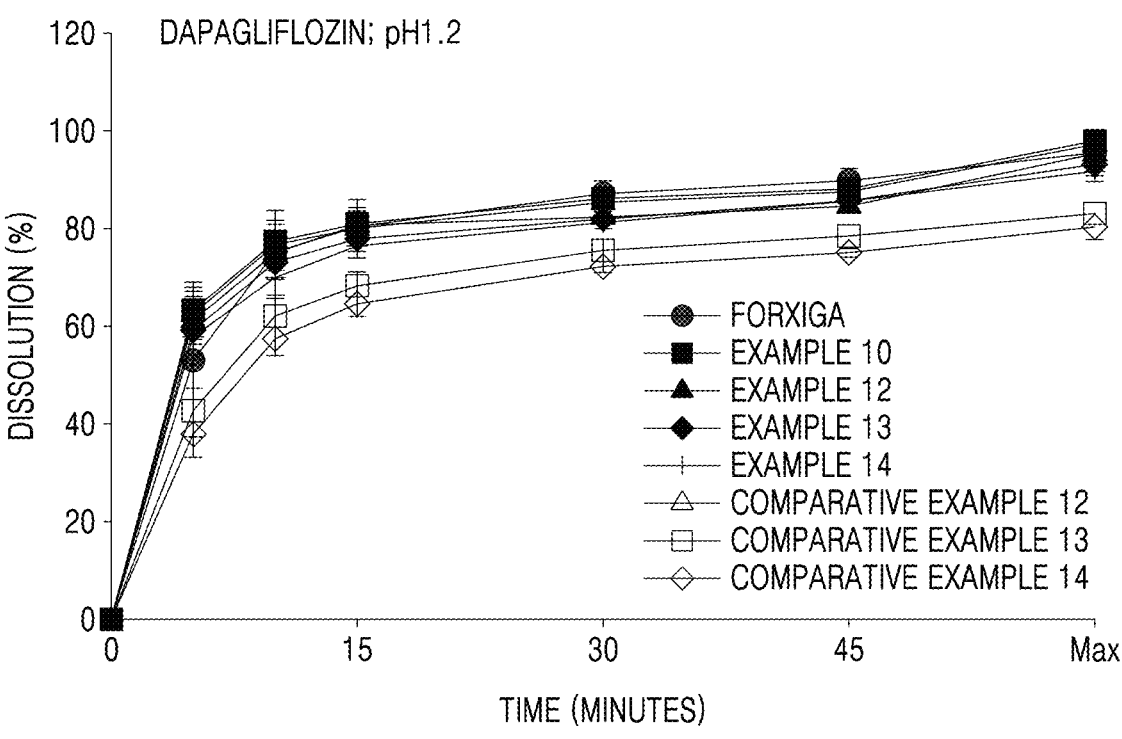

As shown in FIGS. 8 and 9, upon comparison of dissolution patterns of Examples and 12 to 14 and Comparative Examples 12 to 14, in Examples 10 and 12 to 14, each active ingredient was found to show a similar dissolution pattern with a reference drug. As shown in Table 20, in Comparative Example 12, where a PRUV lubricant was not added in the granules, the dissolution pattern was satisfactory, but compacting and sticking (FIG. 11) to rollers occurred in the dry granulation process, thus causing troubles in the apparatus, a low granule yield, and a low productivity. This means that productivity may be improved through the addition of a lubricant during the granulation process. Comparative Examples 13 and 14 correspond to prescriptions with a relatively large amount of PRUV (intragranule content exceeding 5 wt %), and the dissolution was delayed during such overlubrication. In particular, surprisingly, in Comparative Examples 13 and 14, the dissolution rate of the drug was significantly reduced as compared with Example 14, and the dissolution rate was relatively low even at the dissolution point (Max) at which the drug was saturated. This may be a problem for uniform drug administration to patients, and the onset time of the drug may be relatively slow. Therefore, it may be determined that the amount of PRUV may be effective in the range of 1 wt % to 5 wt % in the dry granulation process.

TABLE 20

Granule yield in dry granulation (%)

| | Example 9 | Example 10 | Example 11 | Example 12 | Example 13 | Example 14 |
|---|---|---|---|---|---|---|
| Weight ratio of PRUV in granules (%) | 1 | 1 | 1 | 2 | 3 | 5 |
| Granule yield (%) | 96.8 | 95.9 | 96.7 | 96.1 | 95.1 | 96.2 |

| | Comparative Example 9 | Comparative Example 10 | Comparative Example 11 | Comparative Example 12 | Comparative Example 13 | Comparative Example 14 |
|---|---|---|---|---|---|---|
| Weight ratio of PRUV in granules (%) | 1 | 1 | 1 | 0 | 7 | 8 |
| Granule yield (%) | 97.5 | 96.7 | 94.9 | 75.6 | 95.6 | 96.1 |

Test Example 8: Evaluation of Related Compounds
According to Amount of Lubricant and Excipient An accelerated test was performed and related compounds were evaluated to confirm stability of the formulation with the formulation selected according to Test Example 7. An HDPE bottle containing silica gel was used as a packaging material, and management was carried out in an acceleration chamber.

Figure 12:
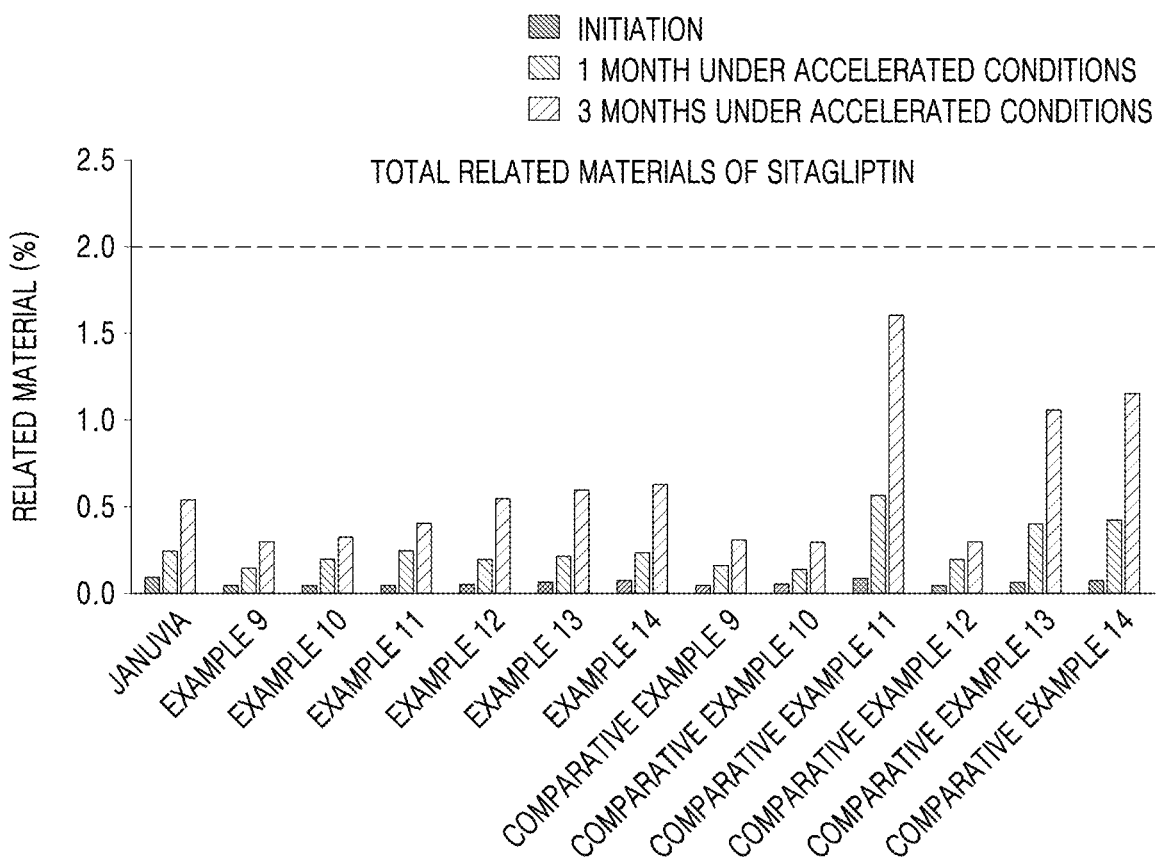
FIG. 12 is a graph showing the results of measurements of the total related compounds (%) of sitagliptin under accelerated conditions of Examples 9 to 14 and Comparative Examples 9 to 14.
Figure 13:
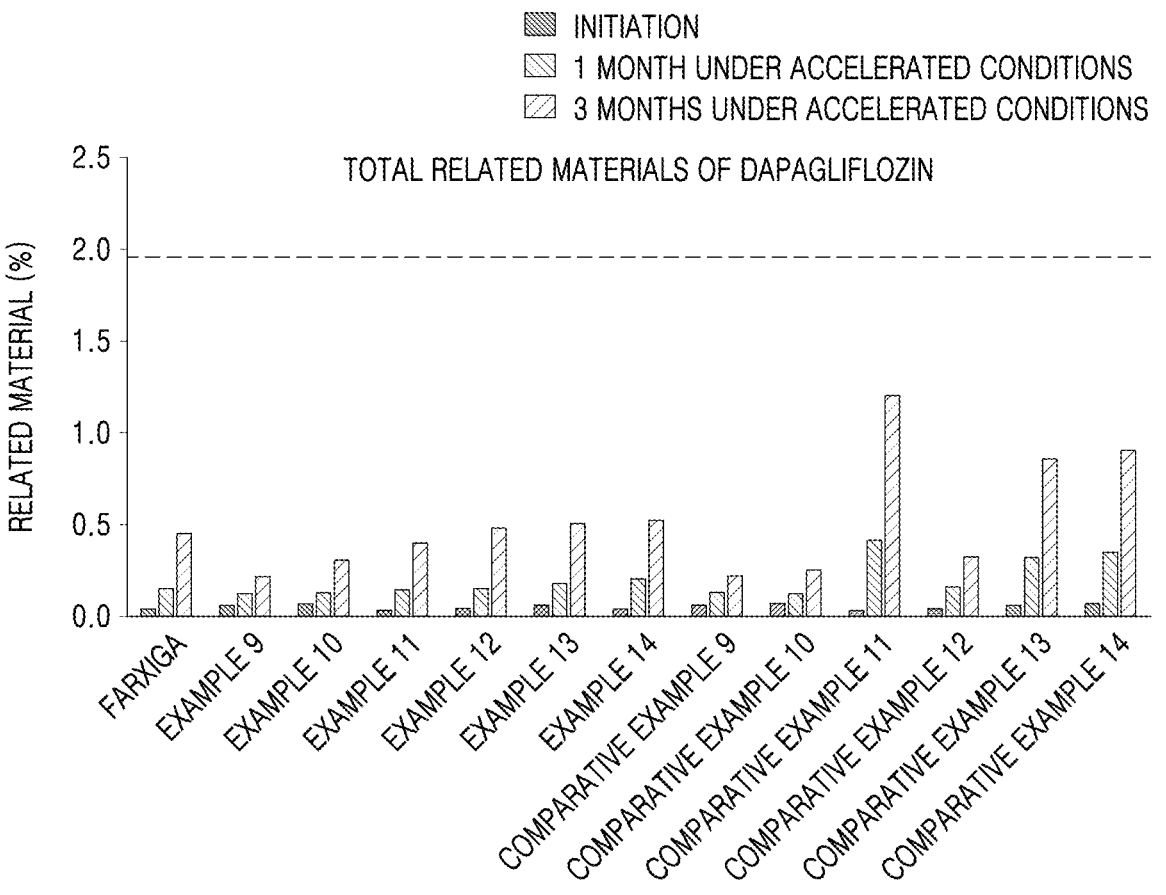
FIG. 13 is a graph showing the results of measurements of the total related compounds (%) of dapagliflozin under accelerated conditions of Examples 9 to 14 and Comparative Examples 9 to 14.

The total related compound (%) of sitagliptin and dapagliflozin of Examples 9 to 14 and Comparative Examples 9 to 14 were measured, and the results are shown in FIGS. 12 and 13.

[Comparison of Total Related Compound Under Accelerated Conditions]

As shown in FIGS. 12 and 13, upon comparison of the total related compound (%) of acceleration stability test in Examples 9 to 14 and Comparative Examples 9 to 14, in Examples 9 to 11, the total related compound of each active ingredient was smaller than that of a reference drug, and thus, the following acceleration stability was also secured. In Examples 12 to 14, the amount of the total related compound was greater than the reference drug, however, the amount was suitable within the standard. In Comparative Example 11 (containing 30 wt % of L-HPC), even when the amount of related compound in 3 months of acceleration was within the standard, the amount of the related compound increased significantly. However, in the following 6 months of acceleration, stability problems may occur even when the product is approved according to the 'Stability Test Standards for Pharmaceuticals'. As compared with other prescriptions, related compounds may be significant and remarkably increases, and thus, it is seen to be an inappropriate pharmaceutical prescription. This is interpreted as indicating water instability due to hygroscopicity due to excessive use of L-HPC. Therefore, according to the data of Test Examples 7 and 8, it was found that L-HPC may be preferably set to 5 wt % to 20 wt % based on the total weight of the tablet.

In addition, it was confirmed that excessive use of PRUV also affects related compounds. When considering Examples 10 and 12 to 14 and Comparative Examples 12 to 14, where the amount of L-HPC in the prescription is constant, in case of Examples and 12 to 14 and Comparative Example 12, the content of the total PRUV relative to the total weight of the tablet was within 3 wt % to 7 wt %, the content of PRUV in the granules was 1 wt % to 5 wt %, and stability was ensured. However, in case of Comparative Examples 13 and 14, PRUV exceeded 5 wt % in the granules relative to the total weight, and the total PRUV content was 7.5 and 10 wt %, respectively, and the production of related compounds was significantly increased, resulting in remarkably low storage stability. This result shows that when the total PRUV is 1 wt % to 7 wt % relative to the total weight of the composite formulation, and the intragranular PRUV content is 1 wt % to 5 wt %, it is suitable for pharmaceutical prescription and at the same time, improved storage stability may be secured.

Test Example 9: Stability Test According to Initial Water Content

Due to the water instability of the active ingredient, based on Example 10 selected according to Test Examples 7 and 8, tablets with different only in water content were prepared, and the stability according to the water content was evaluated.

Compounding compatibility between the formulation and the active ingredient was confirmed, a diluent (microcrystalline cellulose) and disintegrant (croscarmellose sodium) with a relatively wide water standard range of the raw material were selected, and among them, according to the prescription combined according to the water content by batch/grade, the water content and stability aspect were confirmed (according to batch: selected according to the water test result in the manufacturer's report through investigation by batch within the same grade, according to grade: selected according to the water test result in the manufacturer's report of microcrystalline cellulose/croscarmellose sodium through investigation by grade)

By combining each batch/grade of excipient, Examples 10, 15, and 16 and Comparative Examples 15 to 17 were prepared, and the total water content (including surface water and crystal water) per formulation was measured. The water content was measured using the direct titration method using methanol for water measurement as the volume titration method among the water measurement method (Karl Fischer method) among Korean Pharmacopoeia general test methods. The results thereof are shown in Table 21.

Figure 14:
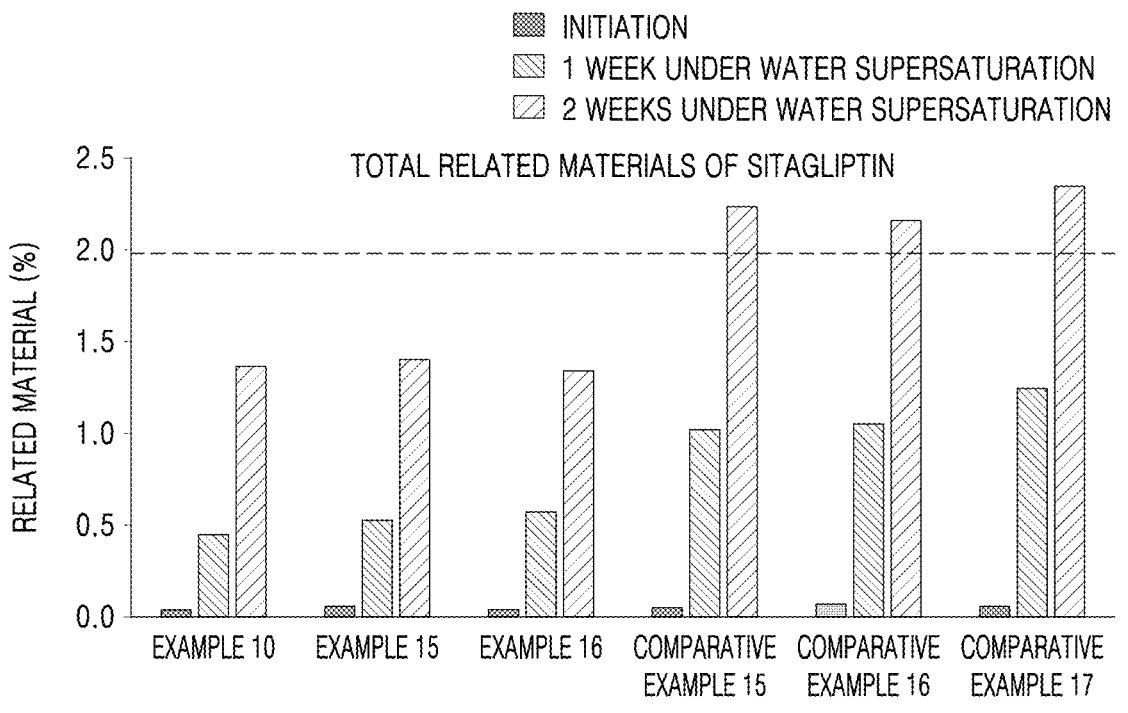
FIG. 14 is a graph showing the results of measurements of the total related compounds (%) of sitagliptin after 1 and 2 weeks in the water supersaturation (25° C. and 90% relative humidity) conditions of Examples 10, 15, and 16 and Comparative Examples 15 to 17 with different water contents in the composite formulation.
Figure 15:
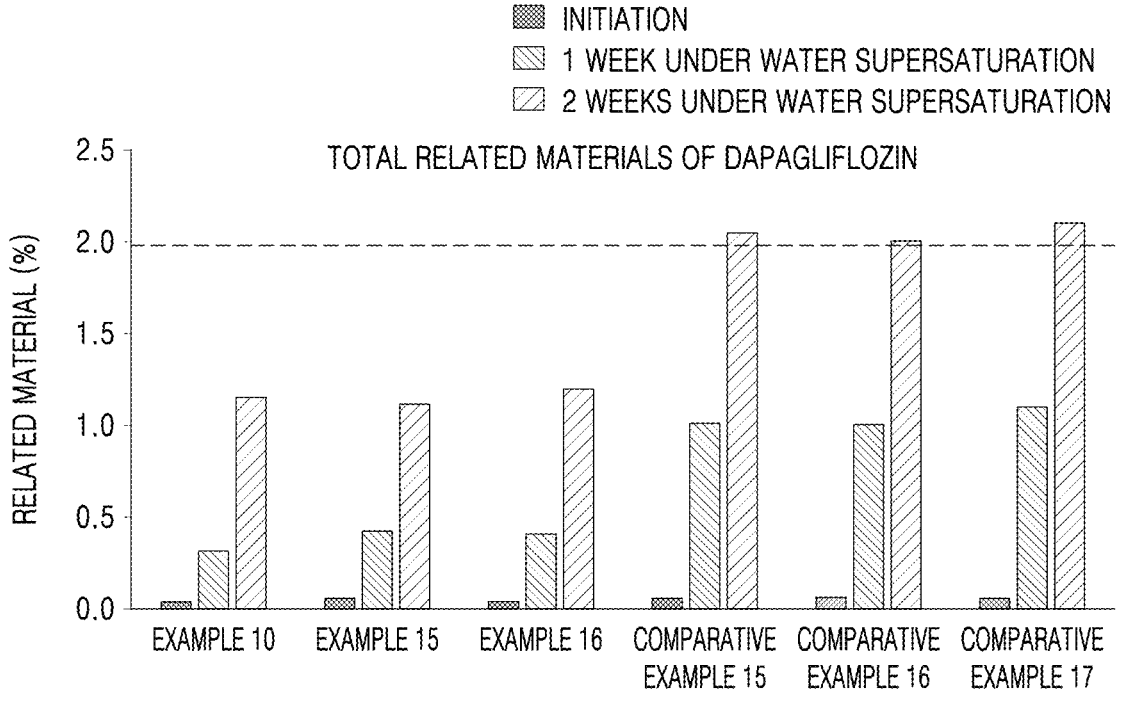
FIG. 15 is a graph showing the results of measurements of the total related compounds (%) of dapagliflozin after 1 and 2 weeks in the water supersaturation (25° C. and 90% relative humidity) conditions of Examples 10, 15, and 16 and Comparative Examples 15 to 17 with different water contents in the composite formulation.

In addition, after storing the formulations of Examples 10, 15, and 16 and Comparative Examples 15 to 17 for 1 and 2 weeks under water supersaturation condition (25° C. and 90% relative humidity), the total related compound (%) of sitagliptin and dapagliflozin were measured. The results thereof are shown in FIGS. 14 and 15.

TABLE 21

| Water content per formulation according to prescription (%) | | | | | | |
|---|---|---|---|---|---|---|
| | Ex-ample 10 | Ex-ample 15 | Ex-ample 16 | Com-parative Ex-ample 10 | Com-parative Ex-ample 15 | Com-parative Ex-ample 16 |
| Microcrystalline cellulose Water content (%) according to batch/grade | 0.5 | 0.5 | 3 | 3 | 5 | 5 |
| Croscarmellose sodium Water content (%) according to batch/grade | 1 | 6 | 1 | 6 | 1 | 6 |
| Total water content (%) | 4.1 | 4.3 | 4.4 | 6.1 | 5.7 | 6.9 |

As a result of water content measurement, in Examples 10, 15, and 16, the total water content per formulation was within about 5%, and in Comparative Examples 15 to 17, the total water content per formulation was 5% or more of water in the initial formulation. As a result of combining a batch/grade with a high water content of the diluent and disintegrant raw materials, the initial total water content was also high.

As a result of storage for 1 and 2 weeks under water supersaturation (25° C., 90% relative humidity) conditions, the amount of related compound significantly increased according to the initial water content. In Comparative Examples 15 to 17, the results exceeded the standard. This result means that a more stable formulation may be designed by controlling the initial water content. In case of selecting raw materials for each batch/grade such that the initial water content is within 5% when designing the formulation, it is possible to manufacture a formulation with improved stability for two active ingredients sensitive to water.

Those skilled in the art will recognize that the disclosure may be embodied in other specific forms without departing from the spirit or essential features thereof. The described embodiments are for illustrative purposes only in all respects and not restrictive. The scope of the disclosure is therefore indicated by the appended claims rather than by the foregoing description. All modifications within the meaning and scope equivalent to the claims are to be embraced within the scope of the disclosure.

The invention claimed is:

1. A composite formulation comprising:

(A) dry granules prepared by dry-granulation using a roller compactor, said dry granules comprising:

a) sitagliptin or a pharmaceutically acceptable salt thereof, or a hydrate thereof;

b) dapagliflozin or a pharmaceutically acceptable salt thereof, or a hydrate thereof; and c) 1 wt % to 5 wt % of sodium stearyl fumarate as a lubricant, based on a total weight of the composite formulation, and (B) additional sodium stearyl fumarate as a lubricant present outside of the dry granules, wherein a total amount of sodium stearyl fumarate present in the composite formulation is 3 wt % to 8 wt %, based on the total weight of the composite formulation.

2. The composite formulation of claim 1, wherein the sitagliptin or a pharmaceutically acceptable salt thereof, or a hydrate thereof, is sitagliptin phosphate hydrate.

3. The composite formulation of claim 1, wherein the dapagliflozin or a pharmaceutically acceptable salt thereof, or a hydrate thereof, is dapagliflozin L-proline or dapagliflozin propanediol.

4. The composite formulation of claim 1, further comprising an excipient selected from microcrystalline cellulose (MCC), mannitol, pregelatinized starch, low-substituted hydroxypropyl cellulose (L-HPC), crospovidone, cross-linked carboxymethyl cellulose sodium (cross-linked CMC Na), and any mixtures thereof.

5. The composite formulation of claim 1, wherein the dry granules further comprise 5 wt % to 20 wt % of low-substituted hydroxypropyl cellulose (L-HPC) as a disintegrant, based on the total weight of the composite formulation.

6. The composite formulation of claim 1, wherein the dry granules further comprise water in an amount of 5 wt % or less, based on the total weight of the composite formulation.

7. The composite formulation of claim 1, wherein the composite formulation is in a form of a tablet, a capsule, or granules.

8. The composite formulation of claim 1, wherein the sitagliptin or a pharmaceutically acceptable salt thereof, or a hydrate thereof, is comprised in an amount of 10 wt % to 40 wt %, based on the total weight of the composite formulation.

9. The composite formulation of claim 1, wherein the dapagliflozin or a pharmaceutically acceptable salt thereof, or a hydrate thereof is comprised in an amount of 2 wt % to 10 wt %, based on the total weight of the composite formulation.

10. The composite formulation of claim 1, further comprising metformin or a pharmaceutically acceptable salt thereof, or a hydrate thereof.

11. A method of preparing the composite formulation of claim 1, the method comprising:

(a) preparing a mixture portion comprising sitagliptin or a pharmaceutically acceptable salt thereof, or a hydrate thereof, and dapagliflozin or a pharmaceutically acceptable salt thereof, or a hydrate thereof, and 1 wt % to 5 wt % of a first portion of sodium stearyl fumarate as a lubricant, based on the total weight of the composite formulation;

(b) dry-granulating the mixture portion using a roller compactor; and (c) further adding a second portion of sodium stearyl fumarate as a lubricant to the granulated material and mixing together, wherein a total amount of sodium stearyl fumarate present in the composite formulation is 3 wt % to 8 wt %, based on the total weight of the composite formulation.

12. The method of claim 11, further comprising tableting the granulated material mixed with sodium stearyl fumarate of step (c).

13. The method of claim 11, wherein the mixture portion further comprises an excipient selected from microcrystalline cellulose (MCC), mannitol, pregelatinized starch, low-substituted hydroxypropyl cellulose (L-HPC), crospovidone, cross-linked carboxymethyl cellulose sodium (cross-linked CMC Na), and any mixtures thereof.

* * * * *